United States Patent
Michelfelder et al.

(10) Patent No.: US 10,640,540 B2
(45) Date of Patent: May 5, 2020

(54) POLYPEPTIDES FOR INHIBITING COMPLEMENT ACTIVATION

(71) Applicant: GREENOVATION BIOTECH GMBH, Freiburg (DE)

(72) Inventors: Stefan Michelfelder, Denzlingen (DE); Karsten Häffner, Freiburg (DE)

(73) Assignee: GREENOVATION BIOTECH GMBH, Freiburg (DE)

( * ) Notice: Subject to any disclaimer, the term of this patent is extended or adjusted under 35 U.S.C. 154(b) by 0 days.

(21) Appl. No.: 16/065,272

(22) PCT Filed: Dec. 23, 2016

(86) PCT No.: PCT/EP2016/082614
§ 371 (c)(1),
(2) Date: Jun. 22, 2018

(87) PCT Pub. No.: WO2017/109208
PCT Pub. Date: Jun. 29, 2017

(65) Prior Publication Data
US 2019/0300589 A1  Oct. 3, 2019

(30) Foreign Application Priority Data
Dec. 23, 2015 (DE) .................. 10 2015 016 665

(51) Int. Cl.
*A61K 38/00* (2006.01)
*C07K 14/47* (2006.01)

(52) U.S. Cl.
CPC ........ *C07K 14/472* (2013.01); *C07K 2319/70* (2013.01); *C07K 2319/74* (2013.01)

(58) Field of Classification Search
None
See application file for complete search history.

(56) References Cited

U.S. PATENT DOCUMENTS

2017/0190753 A1   7/2017   Abache

FOREIGN PATENT DOCUMENTS

WO   WO 2013/142362 A1   9/2013
WO   WO 2015/092335 A2   6/2015

OTHER PUBLICATIONS

Hebecker, The Journal of Immunology, 2013, 191: 1-9 (Year: 2013).*
Skerka, 2013, Molecular immunology, 56, 170-180 (Year: 2013).*
Hebecker, 2013, The Journal of Immunology, 191, 1-10 (Year: 2013).*
Alexander et al., "The simple design of complement factor H: Looks can be deceiving", Molecular Immunology, 2007, vol. 44, pp. 123-132.
Barbour et al., "Recent insights into C3 glomerulopathy", Nephrol Dial Transplant, 2013, vol. 28, pp. 1685-1693.
Blaum et al., "Structural basis for sialic acid—mediated self-recognition by complement factor H", Nature Chemical Biology, Jan. 2015, vol. 11, pp. 77-83. (published online Nov. 24, 2014).
Bomback et al., "Eculizumab for Dense Deposit Disease and C3 Glomerulonephritis", Clin J Am Soc Nephrol, 2012, vol. 7, pp. 748-756.
Braun et al., "Recurrence of Membranoproliferative Glomerulonephritis Type II in Renal Allografts: The North American Pediatric Renal Transplant Cooperative Study Experience", J Am Soc Nephrol, 2005, vol. 16, pp. 2225-2233.
Carroll et al., "Complement in health and disease", Advanced Drug Delivery Reviews, 2011, vol. 63, pp. 965-975.
Cataland et al., "Diagnosis and management of complement mediated thrombotic microangiopathies", Blood Reviews, 2014, vol. 28, pp. 67-74.
Ferreira et al., "Critical Role of the C-Terminal Domains of Factor H in Regulating Complement Activation at Cell Surfaces", J Immunol, 2006, vol. 177, pp. 6308-6316.
Fischer et al., "Regulation der Komplementaktivierung durch ein Fusionsprotein aus funktionellen Domänen von Faktor H verwandtes—Protein 1 und Faktor H", 48. Jahrestagung der Gesellschaft für Pädiatrische Nephrologie, Jan. 1, 2017, XP002767735, pp. 17-18.
Fridkis-Hareli et al., "Design and development of TT30, a novel C3d-targeted C3/C5 convertase inhibitor for treatment of human complement alternative pathway-mediated diseases", Blood, Oct. 27, 2011, vol. 118, No. 17, pp. 4705-4713. (published online Aug. 22, 2011).
Goicoechea de Jorge et al, "Dimerization of complement factor H-related proteins modulates complement activation in vivo", PNAS, Mar. 19, 2013, vol. 110, No. 12, pp. 4685-4690.
Gordon et al, "Identification of Complement Regulatory Domains in Human Factor H", The journal of Immunology, 1995, vol. 155, pp. 348-356.
Häffner et al., "Successful therapy of C3Nef-positive C3 glomerulopathy with plasma therapy and immunosuppression", Pediatr Nephrol, 2015, vol. 30, pp. 1951-1959.
Hebecker et al., "An Engineered Construct Combining Complement Regulatory and Surface-Recognition Domains Represents a Minimal-Size Functional Factor H", The Journal of Immunology, Jun. 14, 2013, vol. 191, total 10 pages.
Herlitz et al., "Pathology after Eculizumab in Dense Deposit Disease and C3 GN", J Am Soc Nephrol, 2012, vol. 23, pp. 1229-1237.
Hillmen et al., "The Complement Inhibitor Eculizumab in Paroxysmal Nocturnal Hemoglobinuria", The New England Journal of Medicine, 2006, vol. 355, No. 12, pp. 1233-1243.

(Continued)

*Primary Examiner* — Satyanarayana R Gudibande
(74) *Attorney, Agent, or Firm* — Birch, Stewart, Kolasch & Birch, LLP

(57) ABSTRACT

The invention relates to a polypeptide comprising a C3 convertase effector domain, a C5 convertase effector domain and optionally a terminal complex inhibitory effector domain which is resistant to deregulation by physiologic FHR-Proteins and has a dimerization motif, and to its therapeutic use.

10 Claims, 5 Drawing Sheets
Specification includes a Sequence Listing.

(56) References Cited

OTHER PUBLICATIONS

Holers, "The spectrum of complement alternative pathway-mediated diseases", Immunological Reviews, 2008, vol. 223; pp. 300-316.
International Search Report, issued in PCT/EP2016/082614, dated Mar. 17, 2017.
Jarva et al., "Regulation of Complement Activation by C-Reactive Protein: Targeting the Complement Inhibitory Activity of Factor H by an Interaction with Short Consensus Repeat Domains 7 and 8-11", J Immunol, 1999, vol. 163, pp. 3957-3962.
Józsi et al., "Attachment of the soluble complement regulator factor H to cell and tissue surfaces: relevance for pathology", Histol Histopathol, 2004, vol. 19, pp. 251-258.
Józsi et al., "Factor H-related proteins determine complement-activating surfaces", Trends in Immunology, Jun. 2015, vol. 36, No. 6, pp. 374-384.
Józsi et al., "The C-terminus of complement factor H is essential for host cell protection", Mol Immunol., Apr. 2007, vol. 44, No. 10, pp. 2697-2706.
Kawa et al., "Complement System in Pathogenesis of AMD: Dual Player in Degeneration and Protection of Retinal Tissue", Journal of Immunology Research, Sep. 4, 2014, vol. 2014, Article ID 483960, total 12 pages.
Legendre et al., "Terminal Complement Inhibitor Eculizumab in Atypical Hemolytic—Uremic Syndrome", N Engl J Med, 2013, vol. 368, pp. 2169-2181.
Licht et al., "Deletion of Lys224 in regulatory domain 4 of Factor H reveals a novel pathomechanism for dense deposit disease (MPGN II)", Kidney International, 2006, vol. 70, pp. 42-50.
Licht et al., "Successful Plasma Therapy for Atypical Hemolytic Uremic Syndrome Caused by Factor H Deficiency Owing to a Novel Mutation in the Complement Cofactor Protein Domain 15", American Journal of Kidney Diseases, Feb. 2005, vol. 45, No. 2, pp. 415-421.
Loirat et al., "Atypical hemolytic uremic syndrome", Orphanet Journal of Rare Diseases, 2011, 6:60, total 30 pages.
Lu et al., "Clinical features and outcomes of 98 children and adults with dense deposit disease", Pediatr Nephrol, May 2012, vol. 27, No, 5, pp. 773-781.
Maillard et al., "Current Understanding of the Role of Complement in IgA Nephropathy", J Am Soc Nephrol, 2015, vol. 26, pp. 1503-1512.
Manuelian et al., "Mutations in factor H reduce binding affinity to C3b and heparin and surface attachment to endothelial cells in hemolytic uremic syndrome", J. Clin. Invest., 2003, vol. 111, No. 8, pp. 1181-1190.
Masani et al., "Update on Membranoproliferative GN", Clin J Am Soc Nephrol, 2014, vol. 9, pp. 600-608.
Mastellos et al., "Compstatin: a C3-targeted complement inhibitor reaching its prime for bedside intervention", Eur J Clin Invest., Apr. 2015, vol. 45, No. 4, pp, 423-440.
Merle et al., "Complement System Part I—Molecular Mechanisms of Activation and Regulation", Frontiers in Immunology, Jun. 2, 2015, vol. 6, Article 262, total 30 pages.
Nichols et al., "An extended mini-complement factor H molecule ameliorates experimental C3 glomerulopathy", Kidney International advance online publication, Jul. 29, 2015, total 9 pages.
Noris et al., "Atypical Hemolytic—Uremic Syndrome", The New England Journal of Medicine, Oct. 22, 2009, vol. 361, No. 17, pp. 1676-1687.
Oppermann et al., "The C-terminus of complement regulator Factor H mediates target recognition: evidence for a compact conformation of the native protein", Clinical and Experimental Immunology, 2006, vol. 144, pp. 342-352.
Parker et al., "Eculizumab", Nature Reviews, Drug Discovery, Jul. 2007, vol. 6, pp. 515-516.
Ricklin et al., "Complement—a key system for immune surveillance and homeostasis", Nat Immunol., Sep. 2010, vol. 11, No. 9, pp. 785-797.
Ricklin et al., "Progress and Trends in Complement Therapeutics", Advances in Experimental Medicine and Biology, 2013, vol. 735, total 22 pages.
Ricklin et al., "Therapeutic control of complement activation at the level of the central component C3", Immunobiology, 2015, total 7 pages.
Rodríguez de Córdoba et al., "Translational Mini-Review Series on Complement Factor H: Genetics and disease associations of human complement factor H", Clinical and Experimental Immunology, 2008, vol. 151, pp. 1-13.
Rodríguez de Córdoba et al., "The human complement factor H: functional roles, genetic variations and disease associations", Molecular Immunology, 2004, vol. 41, pp. 355-367.
Ruseva et al., "Efficacy of Targeted Complement Inhibition in Experimental C3 Glomerulopathy", J Am Soc Nephrol, 2015, vol. 27, total 12 pages.
Schmidt et al., "Rational Engineering of a Minimized Immune Inhibitor with Unique Triple-Targeting Properties", J Immunol, 2013, vol. 190, pp. 5712-5721.
Sethi et al., "Membranoproliferative Glomerulonephritis—A New Look at an Old Entity", N Engl J Med, 2012, vol. 366, pp. 1119-1131.
Skerka et al., "Complement factor H related proteins (CFHRs)", Molecular Immunology, 2013, vol. 56, pp. 170-180.
Skerka et al., "Molecular Cloning of a Human Serum Protein Structurally Related to Complement Factor H", The Journal of Biological Chemistry, 1991, vol. 266, No. 18, Issue of Jun. 25, pp. 12015-12020.
Skerka et al., "Two additional human serum proteins structurally related to complement factor H. Evidence for a family of factor H-related genes", J Immunol, 1992, vol. 148, pp. 3313-3318.
Wagner et al., "Therapeutic potential of complement modulation", Nature Reviews, Drug Discovery, Jan. 2010, vol. 9, pp. 43-56.
Weiler et al., "Control of the amplification convertase of complement by the plasma protein beta1H", Proc. Natl. Acad. Sci. USA, Sep. 1976, vol. 73, No. 9, pp. 3268-3272.
Wilson et al., "Activation of the alternative complement pathway in systemic lupus erythematosus", Clin. exp. Immunol., 1976, vol. 26, pp. 11-20.
Written Opinion of the International Searching Authority, issued in PCT/EP2016/082614, dated Mar. 17, 2017.
Zimmerhackl et al., "Prophylactic Eculizumab after Renal Transplantation in Atypical Hemolytic—Uremic Syndrome", The New England Journal of Medicine, 2010, vol. 362, No. 18, pp. 1746-1748.
Zipfel et al., "Complement regulators and inhibitory proteins", Nature Reviews, Immunology, Oct. 2009, vol. 9, pp. 729-740.
Zuber et al., "Use of eculizumab for atypical haemolytic uraemic syndrome and C3 glomerulopathies", Nat. Rev. Nephrol., 2012, vol. 8, pp. 643-657.
e-meneki.com, "PID (PIDbox of knowledge)", Internet Archive: Wayback Machine, Oct. 1, 2015, URL:http://web.archive.org/web/20151001054747/http://emeneki.com/knowledge/complement_deficiency, pp. 1-4 ( 4 pages).
Heinen et al., "Factor H-related protein 1 (CFHR-1) inhibits complement C5 convertase activity and terminal complex formation", Blood, vol. 114, No. 2, Sep. 17, 2009, pp. 2439-2447 (10 pages).
Holers, "Human C3 glomerulopathy provides unique insights into complement fact H-related protein function", J Clin Invest., vol. 123, No. 6, 2013, pp. 2357-2360 (5 pages).
Japanese Office Action, dated Jul. 2, 2019, for Japanese Application No. 2018-533148, with an English translation.

* cited by examiner

SEQUENCE LISTING

```
<160> NUMBER OF SEQ ID NOS: 9

<210> SEQ ID NO 1
<211> LENGTH: 1231
<212> TYPE: PRT
<213> ORGANISM: homo sapiens

<400> SEQUENCE: 1

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270
```

-continued

```
Pro Asn Gly Asp Tyr Ser Pro Leu Arg Ile Lys His Arg Thr Gly Asp
            275                 280                 285
Glu Ile Thr Tyr Gln Cys Arg Asn Gly Phe Tyr Pro Ala Thr Arg Gly
        290                 295                 300
Asn Thr Ala Lys Cys Thr Ser Thr Gly Trp Ile Pro Ala Pro Arg Cys
305                 310                 315                 320
Thr Leu Lys Pro Cys Asp Tyr Pro Asp Ile Lys His Gly Gly Leu Tyr
                325                 330                 335
His Glu Asn Met Arg Arg Pro Tyr Phe Pro Val Ala Val Gly Lys Tyr
            340                 345                 350
Tyr Ser Tyr Tyr Cys Asp Glu His Phe Glu Thr Pro Ser Gly Ser Tyr
        355                 360                 365
Trp Asp His Ile His Cys Thr Gln Asp Gly Trp Ser Pro Ala Val Pro
370                 375                 380
Cys Leu Arg Lys Cys Tyr Phe Pro Tyr Leu Glu Asn Gly Tyr Asn Gln
385                 390                 395                 400
Asn Tyr Gly Arg Lys Phe Val Gln Gly Lys Ser Ile Asp Val Ala Cys
                405                 410                 415
His Pro Gly Tyr Ala Leu Pro Lys Ala Gln Thr Thr Val Thr Cys Met
            420                 425                 430
Glu Asn Gly Trp Ser Pro Thr Pro Arg Cys Ile Arg Val Lys Thr Cys
        435                 440                 445
Ser Lys Ser Ser Ile Asp Ile Glu Asn Gly Phe Ile Ser Glu Ser Gln
        450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Thr Cys Gly Lys
                485                 490                 495
Asp Gly Trp Ser Ala Gln Pro Thr Cys Ile Lys Ser Cys Asp Ile Pro
            500                 505                 510
Val Phe Met Asn Ala Arg Thr Lys Asn Asp Phe Thr Trp Phe Lys Leu
        515                 520                 525
Asn Asp Thr Leu Asp Tyr Glu Cys His Asp Gly Tyr Glu Ser Asn Thr
530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
            580                 585                 590
Leu Lys Phe Ser Cys Lys Pro Gly Phe Thr Ile Val Gly Pro Asn Ser
        595                 600                 605
Val Gln Cys Tyr His Phe Gly Leu Ser Pro Asp Leu Pro Ile Cys Lys
610                 615                 620
Glu Gln Val Gln Ser Cys Gly Pro Pro Glu Leu Leu Asn Gly Asn
625                 630                 635                 640
Val Lys Glu Lys Thr Lys Glu Glu Tyr Gly His Ser Glu Val Val Glu
                645                 650                 655
Tyr Tyr Cys Asn Pro Arg Phe Leu Met Lys Gly Pro Asn Lys Ile Gln
            660                 665                 670
Cys Val Asp Gly Glu Trp Thr Thr Leu Pro Val Cys Ile Val Glu Glu
        675                 680                 685
Ser Thr Cys Gly Asp Ile Pro Glu Leu Glu His Gly Trp Ala Gln Leu
```

-continued

```
            690                 695                 700
Ser Ser Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
                740                 745                 750

Cys Lys Ser Ser Asn Leu Ile Ile Leu Glu Glu His Leu Lys Asn Lys
                755                 760                 765

Lys Glu Phe Asp His Asn Ser Asn Ile Arg Tyr Arg Cys Arg Gly Lys
770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Gln
                805                 810                 815

Ile Pro Asn Ser His Asn Met Thr Thr Thr Leu Asn Tyr Arg Asp Gly
                820                 825                 830

Glu Lys Val Ser Val Leu Cys Gln Glu Asn Tyr Leu Ile Gln Glu Gly
                835                 840                 845

Glu Glu Ile Thr Cys Lys Asp Gly Arg Trp Gln Ser Ile Pro Leu Cys
850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Pro Pro Gln Cys Glu Gly
                915                 920                 925

Leu Pro Cys Lys Ser Pro Pro Glu Ile Ser His Gly Val Val Ala His
                930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro Met Gly Glu Lys Lys Asp Val Tyr
                995                 1000                1005

Lys Ala Gly Glu Gln Val Thr Tyr Thr Cys Ala Thr Tyr Tyr Lys
                1010                1015                1020

Met Asp Gly Ala Ser Asn Val Thr Cys Ile Asn Ser Arg Trp Thr
                1025                1030                1035

Gly Arg Pro Thr Cys Arg Asp Thr Ser Cys Val Asn Pro Pro Thr
                1040                1045                1050

Val Gln Asn Ala Tyr Ile Val Ser Arg Gln Met Ser Lys Tyr Pro
                1055                1060                1065

Ser Gly Glu Arg Val Arg Tyr Gln Cys Arg Ser Pro Tyr Glu Met
                1070                1075                1080

Phe Gly Asp Glu Glu Val Met Cys Leu Asn Gly Asn Trp Thr Glu
                1085                1090                1095

Pro Pro Gln Cys Lys Asp Ser Thr Gly Lys Cys Gly Pro Pro Pro
                1100                1105                1110
```

```
Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 2
<211> LENGTH: 330
<212> TYPE: PRT
<213> ORGANISM: Homo sapiens

<400> SEQUENCE: 2

Met Trp Leu Leu Val Ser Val Ile Leu Ile Ser Arg Ile Ser Ser Val
1               5                   10                  15

Gly Gly Glu Ala Thr Phe Cys Asp Phe Pro Lys Ile Asn His Gly Ile
            20                  25                  30

Leu Tyr Asp Glu Glu Lys Tyr Lys Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Thr Glu Glu Gly Trp Ser Pro Thr
65                  70                  75                  80

Pro Lys Cys Leu Arg Leu Cys Phe Phe Pro Phe Val Glu Asn Gly His
                85                  90                  95

Ser Glu Ser Ser Gly Gln Thr His Leu Glu Gly Asp Thr Val Gln Ile
            100                 105                 110

Ile Cys Asn Thr Gly Tyr Arg Leu Gln Asn Asn Glu Asn Asn Ile Ser
        115                 120                 125

Cys Val Glu Arg Gly Trp Ser Thr Pro Pro Lys Cys Arg Ser Thr Asp
    130                 135                 140

Thr Ser Cys Val Asn Pro Pro Thr Val Gln Asn Ala His Ile Leu Ser
145                 150                 155                 160

Arg Gln Met Ser Lys Tyr Pro Ser Gly Glu Arg Val Arg Tyr Glu Cys
                165                 170                 175

Arg Ser Pro Tyr Glu Met Phe Gly Asp Glu Glu Val Met Cys Leu Asn
            180                 185                 190

Gly Asn Trp Thr Glu Pro Pro Gln Cys Lys Asp Ser Thr Gly Lys Cys
        195                 200                 205

Gly Pro Pro Pro Pro Ile Asp Asn Gly Asp Ile Thr Ser Phe Pro Leu
    210                 215                 220

Ser Val Tyr Ala Pro Ala Ser Ser Val Glu Tyr Gln Cys Gln Asn Leu
225                 230                 235                 240

Tyr Gln Leu Glu Gly Asn Lys Arg Ile Thr Cys Arg Asn Gly Gln Trp
```

```
                    245                 250                 255

Ser Glu Pro Pro Lys Cys Leu His Pro Cys Val Ile Ser Arg Glu Ile
                260                 265                 270

Met Glu Asn Tyr Asn Ile Ala Leu Arg Trp Thr Ala Lys Gln Lys Leu
            275                 280                 285

Tyr Leu Arg Thr Gly Glu Ser Ala Glu Phe Val Cys Lys Arg Gly Tyr
        290                 295                 300

Arg Leu Ser Ser Arg Ser His Thr Leu Arg Thr Thr Cys Trp Asp Gly
305                 310                 315                 320

Lys Leu Glu Tyr Pro Thr Cys Ala Lys Arg
                325                 330

<210> SEQ ID NO 3
<211> LENGTH: 270
<212> TYPE: PRT
<213> ORGANISM: Homo sapiens

<400> SEQUENCE: 3

Met Trp Leu Leu Val Ser Val Ile Leu Ile Ser Arg Ile Ser Ser Val
1               5                   10                  15

Gly Gly Glu Ala Met Phe Cys Asp Phe Pro Lys Ile Asn His Gly Ile
            20                  25                  30

Leu Tyr Asp Glu Glu Lys Tyr Lys Pro Phe Ser Gln Val Pro Thr Gly
        35                  40                  45

Glu Val Phe Tyr Tyr Ser Cys Glu Tyr Asn Phe Val Ser Pro Ser Lys
    50                  55                  60

Ser Phe Trp Thr Arg Ile Thr Cys Ala Glu Gly Trp Ser Pro Thr
65                  70                  75                  80

Pro Lys Cys Leu Arg Leu Cys Phe Phe Pro Phe Val Glu Asn Gly His
                85                  90                  95

Ser Glu Ser Ser Gly Gln Thr His Leu Glu Gly Asp Thr Val Gln Ile
            100                 105                 110

Ile Cys Asn Thr Gly Tyr Arg Leu Gln Asn Asn Glu Asn Asn Ile Ser
        115                 120                 125

Cys Val Glu Arg Gly Trp Ser Thr Pro Pro Lys Cys Arg Ser Thr Ile
    130                 135                 140

Ser Ala Glu Lys Cys Gly Pro Pro Pro Ile Asp Asn Gly Asp Ile
145                 150                 155                 160

Thr Ser Phe Leu Leu Ser Val Tyr Ala Pro Gly Ser Ser Val Glu Tyr
                165                 170                 175

Gln Cys Gln Asn Leu Tyr Gln Leu Glu Gly Asn Asn Gln Ile Thr Cys
            180                 185                 190

Arg Asn Gly Gln Trp Ser Glu Pro Pro Lys Cys Leu Asp Pro Cys Val
        195                 200                 205

Ile Ser Gln Glu Ile Met Glu Lys Tyr Asn Ile Lys Leu Lys Trp Thr
    210                 215                 220

Asn Gln Gln Lys Leu Tyr Ser Arg Thr Gly Asp Ile Val Glu Phe Val
225                 230                 235                 240

Cys Lys Ser Gly Tyr His Pro Thr Lys Ser His Ser Phe Arg Ala Met
                245                 250                 255

Cys Gln Asn Gly Lys Leu Val Tyr Pro Ser Cys Glu Glu Lys
            260                 265                 270

<210> SEQ ID NO 4
<211> LENGTH: 386
```

<212> TYPE: PRT
<213> ORGANISM: Artificial Sequence
<220> FEATURE:
<223> OTHER INFORMATION: construct 10His-MMFHR1

<400> SEQUENCE: 4

```
Ala Asp Leu Gly Ser His His His His His His His His His Asp
1               5                   10                  15

Tyr Asp Arg Ser Phe Cys Asp Phe Pro Lys Ile Asn His Gly Ile Leu
                20                  25                  30

Tyr Asp Glu Glu Lys Tyr Lys Pro Phe Ser Gln Val Pro Thr Gly Glu
            35                  40                  45

Val Phe Tyr Tyr Ser Cys Glu Tyr Asn Phe Val Ser Pro Ser Lys Ser
    50                  55                  60

Phe Trp Thr Arg Ile Thr Cys Thr Glu Glu Gly Trp Ser Pro Thr Pro
65                  70                  75                  80

Lys Cys Leu Arg Leu Cys Phe Phe Pro Phe Val Glu Asn Gly His Ser
                85                  90                  95

Glu Ser Ser Gly Gln Thr His Leu Glu Gly Asp Thr Val Gln Ile Ile
                100                 105                 110

Cys Asn Thr Gly Tyr Arg Leu Gln Asn Asn Glu Asn Asn Ile Ser Cys
            115                 120                 125

Val Glu Arg Gly Trp Ser Thr Pro Pro Lys Cys Arg Ser Glu Asp Cys
130                 135                 140

Asn Glu Leu Pro Pro Arg Arg Asn Thr Glu Ile Leu Thr Gly Ser Trp
145                 150                 155                 160

Ser Asp Gln Thr Tyr Pro Glu Gly Thr Gln Ala Ile Tyr Lys Cys Arg
                165                 170                 175

Pro Gly Tyr Arg Ser Leu Gly Asn Val Ile Met Val Cys Arg Lys Gly
            180                 185                 190

Glu Trp Val Ala Leu Asn Pro Leu Arg Lys Cys Gln Lys Arg Pro Cys
        195                 200                 205

Gly His Pro Gly Asp Thr Pro Phe Gly Thr Phe Thr Leu Thr Gly Gly
    210                 215                 220

Asn Val Phe Glu Tyr Gly Val Lys Ala Val Tyr Thr Cys Asn Glu Gly
225                 230                 235                 240

Tyr Gln Leu Leu Gly Glu Ile Asn Tyr Arg Glu Cys Asp Thr Asp Gly
                245                 250                 255

Trp Thr Asn Asp Ile Pro Ile Cys Glu Val Val Lys Cys Leu Pro Val
            260                 265                 270

Thr Ala Pro Glu Asn Gly Lys Ile Val Ser Ser Ala Met Glu Pro Asp
        275                 280                 285

Arg Glu Tyr His Phe Gly Gln Ala Val Arg Phe Val Cys Asn Ser Gly
    290                 295                 300

Tyr Lys Ile Glu Gly Asp Glu Glu Met His Cys Ser Asp Asp Gly Phe
305                 310                 315                 320

Trp Ser Lys Glu Lys Pro Lys Cys Val Glu Ile Ser Cys Lys Ser Pro
                325                 330                 335

Asp Val Ile Asn Gly Ser Pro Ile Ser Gln Lys Ile Ile Tyr Lys Glu
            340                 345                 350

Asn Glu Arg Phe Gln Tyr Lys Cys Asn Met Gly Tyr Glu Tyr Ser Glu
        355                 360                 365

Arg Gly Asp Ala Val Cys Thr Glu Ser Gly Trp Arg Pro Leu Pro Ser
    370                 375                 380
```

Cys Glu
385

<210> SEQ ID NO 5
<211> LENGTH: 366
<212> TYPE: PRT
<213> ORGANISM: Artificial Sequence
<220> FEATURE:
<223> OTHER INFORMATION: Construct MMFHR1

<400> SEQUENCE: 5

```
Phe Cys Asp Phe Pro Lys Ile Asn His Gly Ile Leu Tyr Asp Glu Glu
1               5                   10                  15

Lys Tyr Lys Pro Phe Ser Gln Val Pro Thr Gly Glu Val Phe Tyr Tyr
            20                  25                  30

Ser Cys Glu Tyr Asn Phe Val Ser Pro Ser Lys Ser Phe Trp Thr Arg
        35                  40                  45

Ile Thr Cys Thr Glu Glu Gly Trp Ser Pro Thr Pro Lys Cys Leu Arg
    50                  55                  60

Leu Cys Phe Phe Pro Phe Val Glu Asn Gly His Ser Glu Ser Ser Gly
65                  70                  75                  80

Gln Thr His Leu Glu Gly Asp Thr Val Gln Ile Ile Cys Asn Thr Gly
                85                  90                  95

Tyr Arg Leu Gln Asn Asn Glu Asn Asn Ile Ser Cys Val Glu Arg Gly
            100                 105                 110

Trp Ser Thr Pro Pro Lys Cys Arg Ser Glu Asp Cys Asn Glu Leu Pro
        115                 120                 125

Pro Arg Arg Asn Thr Glu Ile Leu Thr Gly Ser Trp Ser Asp Gln Thr
    130                 135                 140

Tyr Pro Glu Gly Thr Gln Ala Ile Tyr Lys Cys Arg Pro Gly Tyr Arg
145                 150                 155                 160

Ser Leu Gly Asn Val Ile Met Val Cys Arg Lys Gly Glu Trp Val Ala
                165                 170                 175

Leu Asn Pro Leu Arg Lys Cys Gln Lys Arg Pro Cys Gly His Pro Gly
            180                 185                 190

Asp Thr Pro Phe Gly Thr Phe Thr Leu Thr Gly Gly Asn Val Phe Glu
        195                 200                 205

Tyr Gly Val Lys Ala Val Tyr Thr Cys Asn Glu Gly Tyr Gln Leu Leu
    210                 215                 220

Gly Glu Ile Asn Tyr Arg Glu Cys Asp Thr Asp Gly Trp Thr Asn Asp
225                 230                 235                 240

Ile Pro Ile Cys Glu Val Val Lys Cys Leu Pro Val Thr Ala Pro Glu
                245                 250                 255

Asn Gly Lys Ile Val Ser Ser Ala Met Glu Pro Asp Arg Glu Tyr His
            260                 265                 270

Phe Gly Gln Ala Val Arg Phe Val Cys Asn Ser Gly Tyr Lys Ile Glu
        275                 280                 285

Gly Asp Glu Glu Met His Cys Ser Asp Gly Phe Trp Ser Lys Glu
    290                 295                 300

Lys Pro Lys Cys Val Glu Ile Ser Cys Lys Ser Pro Asp Val Ile Asn
305                 310                 315                 320

Gly Ser Pro Ile Ser Gln Lys Ile Ile Tyr Lys Glu Asn Glu Arg Phe
                325                 330                 335

Gln Tyr Lys Cys Asn Met Gly Tyr Glu Tyr Ser Glu Arg Gly Asp Ala
            340                 345                 350
```

Val Cys Thr Glu Ser Gly Trp Arg Pro Leu Pro Ser Cys Glu
            355                 360                 365

<210> SEQ ID NO 6
<211> LENGTH: 392
<212> TYPE: PRT
<213> ORGANISM: Artificial Sequence
<220> FEATURE:
<223> OTHER INFORMATION: Construct 10His-FHR1-2

<400> SEQUENCE: 6

Ala Asp Leu Gly Ser His His His His His His His His His Asp
1               5                   10                  15

Tyr Asp Arg Ser Phe Cys Asp Phe Pro Lys Ile Asn His Gly Ile Leu
            20                  25                  30

Tyr Asp Glu Glu Lys Tyr Lys Pro Phe Ser Gln Val Pro Thr Gly Glu
            35                  40                  45

Val Phe Tyr Tyr Ser Cys Glu Tyr Asn Phe Val Ser Pro Ser Lys Ser
50              55                  60

Phe Trp Thr Arg Ile Thr Cys Thr Glu Glu Gly Trp Ser Pro Thr Pro
65              70                  75                  80

Lys Cys Leu Arg Leu Cys Phe Phe Pro Phe Val Glu Asn Gly His Ser
            85                  90                  95

Glu Ser Ser Gly Gln Thr His Leu Glu Gly Asp Thr Val Gln Ile Ile
            100                 105                 110

Cys Asn Thr Gly Tyr Arg Leu Gln Asn Asn Glu Asn Asn Ile Ser Cys
            115                 120                 125

Val Glu Arg Gly Trp Ser Thr Pro Pro Lys Cys Arg Ser Glu Ala Met
130             135                 140

Phe Cys Asp Phe Pro Lys Ile Asn His Gly Ile Leu Tyr Asp Glu Glu
145                 150                 155                 160

Lys Tyr Lys Pro Phe Ser Gln Val Pro Thr Gly Glu Val Phe Tyr Tyr
            165                 170                 175

Ser Cys Glu Tyr Asn Phe Val Ser Pro Ser Lys Ser Phe Trp Thr Arg
            180                 185                 190

Ile Thr Cys Ala Glu Glu Gly Trp Ser Pro Thr Pro Lys Cys Leu Arg
            195                 200                 205

Leu Cys Phe Phe Pro Phe Val Glu Asn Gly His Ser Glu Ser Ser Gly
            210                 215                 220

Gln Thr His Leu Glu Gly Thr Val Gln Ile Ile Cys Asn Thr Gly Tyr
225                 230                 235                 240

Arg Leu Gln Asn Asn Glu Asn Asn Ile Ser Cys Val Glu Arg Gly Trp
            245                 250                 255

Ser Thr Pro Pro Lys Cys Arg Ser Thr Ile Ser Ala Glu Lys Cys Gly
            260                 265                 270

Pro Pro Pro Pro Ile Asp Asn Gly Asp Ile Thr Ser Phe Leu Leu Ser
            275                 280                 285

Val Tyr Ala Pro Gly Ser Ser Val Glu Tyr Gln Cys Gln Asn Leu Tyr
            290                 295                 300

Gln Leu Glu Gly Asn Asn Gln Ile Thr Cys Arg Asn Gly Gln Trp Ser
305                 310                 315                 320

Glu Pro Pro Lys Cys Leu Asp Pro Cys Val Ile Ser Gln Glu Ile Met
            325                 330                 335

Glu Lys Tyr Asn Ile Lys Leu Lys Trp Thr Asn Gln Gln Lys Leu Tyr
            340                 345                 350

Ser Arg Thr Gly Asp Ile Val Glu Phe Val Cys Lys Ser Gly Tyr His
        355                 360                 365

Pro Thr Lys Ser His Ser Phe Arg Ala Met Cys Gln Asn Gly Lys Leu
        370                 375                 380

Val Tyr Pro Ser Cys Glu Glu Lys
385                 390

<210> SEQ ID NO 7
<211> LENGTH: 372
<212> TYPE: PRT
<213> ORGANISM: Artificial Sequence
<220> FEATURE:
<223> OTHER INFORMATION: Construct FHR1-2

<400> SEQUENCE: 7

Phe Cys Asp Phe Pro Lys Ile Asn His Gly Ile Leu Tyr Asp Glu Glu
1               5                   10                  15

Lys Tyr Lys Pro Phe Ser Gln Val Pro Thr Gly Glu Val Phe Tyr Tyr
                20                  25                  30

Ser Cys Glu Tyr Asn Phe Val Ser Pro Ser Lys Ser Phe Trp Thr Arg
            35                  40                  45

Ile Thr Cys Thr Glu Glu Gly Trp Ser Pro Thr Pro Lys Cys Leu Arg
        50                  55                  60

Leu Cys Phe Phe Pro Phe Val Glu Asn Gly His Ser Glu Ser Ser Gly
65                  70                  75                  80

Gln Thr His Leu Glu Gly Asp Thr Val Gln Ile Ile Cys Asn Thr Gly
                85                  90                  95

Tyr Arg Leu Gln Asn Asn Glu Asn Asn Ile Ser Cys Val Glu Arg Gly
            100                 105                 110

Trp Ser Thr Pro Pro Lys Cys Arg Ser Glu Ala Met Phe Cys Asp Phe
        115                 120                 125

Pro Lys Ile Asn His Gly Ile Leu Tyr Asp Glu Glu Lys Tyr Lys Pro
    130                 135                 140

Phe Ser Gln Val Pro Thr Gly Glu Val Phe Tyr Tyr Ser Cys Glu Tyr
145                 150                 155                 160

Asn Phe Val Ser Pro Ser Lys Ser Phe Trp Thr Arg Ile Thr Cys Ala
                165                 170                 175

Glu Glu Gly Trp Ser Pro Thr Pro Lys Cys Leu Arg Leu Cys Phe Phe
            180                 185                 190

Pro Phe Val Glu Asn Gly His Ser Glu Ser Ser Gly Gln Thr His Leu
        195                 200                 205

Glu Gly Thr Val Gln Ile Ile Cys Asn Thr Gly Tyr Arg Leu Gln Asn
    210                 215                 220

Asn Glu Asn Asn Ile Ser Cys Val Glu Arg Gly Trp Ser Thr Pro Pro
225                 230                 235                 240

Lys Cys Arg Ser Thr Ile Ser Ala Glu Lys Cys Gly Pro Pro Pro Pro
                245                 250                 255

Ile Asp Asn Gly Asp Ile Thr Ser Phe Leu Leu Ser Val Tyr Ala Pro
            260                 265                 270

Gly Ser Ser Val Glu Tyr Gln Cys Gln Asn Leu Tyr Gln Leu Glu Gly
        275                 280                 285

Asn Asn Gln Ile Thr Cys Arg Asn Gly Gln Trp Ser Glu Pro Pro Lys
    290                 295                 300

Cys Leu Asp Pro Cys Val Ile Ser Gln Glu Ile Met Glu Lys Tyr Asn
305                 310                 315                 320

-continued

```
Ile Lys Leu Lys Trp Thr Asn Gln Gln Lys Leu Tyr Ser Arg Thr Gly
            325                 330                 335

Asp Ile Val Glu Phe Val Cys Lys Ser Gly Tyr His Pro Thr Lys Ser
        340                 345                 350

His Ser Phe Arg Ala Met Cys Gln Asn Gly Lys Leu Val Tyr Pro Ser
        355                 360                 365

Cys Glu Glu Lys
        370

<210> SEQ ID NO 8
<211> LENGTH: 514
<212> TYPE: PRT
<213> ORGANISM: Artificial Sequence
<220> FEATURE:
<223> OTHER INFORMATION: Construct 10His-MFHR1

<400> SEQUENCE: 8

Ala Asp Leu Gly Ser His His His His His His His His His Asp
1               5                   10                  15

Tyr Asp Arg Ser Phe Cys Asp Phe Pro Lys Ile Asn His Gly Ile Leu
            20                  25                  30

Tyr Asp Glu Glu Lys Tyr Lys Pro Phe Ser Gln Val Pro Thr Gly Glu
        35                  40                  45

Val Phe Tyr Tyr Ser Cys Glu Tyr Asn Phe Val Ser Pro Ser Lys Ser
    50                  55                  60

Phe Trp Thr Arg Ile Thr Cys Thr Glu Glu Gly Trp Ser Pro Thr Pro
65                  70                  75                  80

Lys Cys Leu Arg Leu Cys Phe Phe Pro Phe Val Glu Asn Gly His Ser
                85                  90                  95

Glu Ser Ser Gly Gln Thr His Leu Glu Gly Asp Thr Val Gln Ile Ile
            100                 105                 110

Cys Asn Thr Gly Tyr Arg Leu Gln Asn Asn Glu Asn Asn Ile Ser Cys
        115                 120                 125

Val Glu Arg Gly Trp Ser Thr Pro Pro Lys Cys Arg Ser Glu Asp Cys
    130                 135                 140

Asn Glu Leu Pro Pro Arg Arg Asn Thr Glu Ile Leu Thr Gly Ser Trp
145                 150                 155                 160

Ser Asp Gln Thr Tyr Pro Glu Gly Thr Gln Ala Ile Tyr Lys Cys Arg
                165                 170                 175

Pro Gly Tyr Arg Ser Leu Gly Asn Val Ile Met Val Cys Arg Lys Gly
            180                 185                 190

Glu Trp Val Ala Leu Asn Pro Leu Arg Lys Cys Gln Lys Arg Pro Cys
        195                 200                 205

Gly His Pro Gly Asp Thr Pro Phe Gly Thr Phe Thr Leu Thr Gly Gly
    210                 215                 220

Asn Val Phe Glu Tyr Gly Val Lys Ala Val Tyr Thr Cys Asn Glu Gly
225                 230                 235                 240

Tyr Gln Leu Leu Gly Glu Ile Asn Tyr Arg Glu Cys Asp Thr Asp Gly
                245                 250                 255

Trp Thr Asn Asp Ile Pro Ile Cys Glu Val Val Lys Cys Leu Pro Val
            260                 265                 270

Thr Ala Pro Glu Asn Gly Lys Ile Val Ser Ser Ala Met Glu Pro Asp
        275                 280                 285

Arg Glu Tyr His Phe Gly Gln Ala Val Arg Phe Val Cys Asn Ser Gly
    290                 295                 300
```

```
Tyr Lys Ile Glu Gly Asp Glu Glu Met His Cys Ser Asp Asp Gly Phe
305                 310                 315                 320

Trp Ser Lys Glu Lys Pro Lys Cys Val Glu Ile Ser Cys Lys Ser Pro
                325                 330                 335

Asp Val Ile Asn Gly Ser Pro Ile Ser Gln Lys Ile Ile Tyr Lys Glu
            340                 345                 350

Asn Glu Arg Phe Gln Tyr Lys Cys Asn Met Gly Tyr Glu Tyr Ser Glu
        355                 360                 365

Arg Gly Asp Ala Val Cys Thr Glu Ser Gly Trp Arg Pro Leu Pro Ser
370                 375                 380

Cys Glu Asp Ser Thr Gly Lys Cys Gly Pro Pro Pro Pro Ile Asp Asn
385                 390                 395                 400

Gly Asp Ile Thr Ser Phe Pro Leu Ser Val Tyr Ala Pro Ala Ser Ser
            405                 410                 415

Val Glu Tyr Gln Cys Gln Asn Leu Tyr Gln Leu Glu Gly Asn Lys Arg
        420                 425                 430

Ile Thr Cys Arg Asn Gly Gln Trp Ser Glu Pro Pro Lys Cys Leu His
    435                 440                 445

Pro Cys Val Ile Ser Arg Glu Ile Met Glu Asn Tyr Asn Ile Ala Leu
450                 455                 460

Arg Trp Thr Ala Lys Gln Lys Leu Tyr Ser Arg Thr Gly Glu Ser Val
465                 470                 475                 480

Glu Phe Val Cys Lys Arg Gly Tyr Arg Leu Ser Ser Arg Ser His Thr
                485                 490                 495

Leu Arg Thr Thr Cys Trp Asp Gly Lys Leu Glu Tyr Pro Thr Cys Ala
            500                 505                 510

Lys Arg

<210> SEQ ID NO 9
<211> LENGTH: 494
<212> TYPE: PRT
<213> ORGANISM: Artificial Sequence
<220> FEATURE:
<223> OTHER INFORMATION: Construct MFHR1

<400> SEQUENCE: 9

Phe Cys Asp Phe Pro Lys Ile Asn His Gly Ile Leu Tyr Asp Glu Glu
1               5                   10                  15

Lys Tyr Lys Pro Phe Ser Gln Val Pro Thr Gly Glu Val Phe Tyr Tyr
                20                  25                  30

Ser Cys Glu Tyr Asn Phe Val Ser Pro Ser Lys Ser Phe Trp Thr Arg
            35                  40                  45

Ile Thr Cys Thr Glu Glu Gly Trp Ser Pro Thr Pro Lys Cys Leu Arg
    50                  55                  60

Leu Cys Phe Phe Pro Phe Val Glu Asn Gly His Ser Glu Ser Ser Gly
65                  70                  75                  80

Gln Thr His Leu Glu Gly Asp Thr Val Gln Ile Ile Cys Asn Thr Gly
                85                  90                  95

Tyr Arg Leu Gln Asn Asn Glu Asn Asn Ile Ser Cys Val Glu Arg Gly
            100                 105                 110

Trp Ser Thr Pro Pro Lys Cys Arg Ser Glu Asp Cys Asn Glu Leu Pro
        115                 120                 125

Pro Arg Arg Asn Thr Glu Ile Leu Thr Gly Ser Trp Ser Asp Gln Thr
    130                 135                 140

Tyr Pro Glu Gly Thr Gln Ala Ile Tyr Lys Cys Arg Pro Gly Tyr Arg
```

```
145                 150                 155                 160
Ser Leu Gly Asn Val Ile Met Val Cys Arg Lys Gly Glu Trp Val Ala
                165                 170                 175

Leu Asn Pro Leu Arg Lys Cys Gln Lys Arg Pro Cys Gly His Pro Gly
                180                 185                 190

Asp Thr Pro Phe Gly Thr Phe Thr Leu Thr Gly Gly Asn Val Phe Glu
                195                 200                 205

Tyr Gly Val Lys Ala Val Tyr Thr Cys Asn Glu Gly Tyr Gln Leu Leu
                210                 215                 220

Gly Glu Ile Asn Tyr Arg Glu Cys Asp Thr Asp Gly Trp Thr Asn Asp
225                 230                 235                 240

Ile Pro Ile Cys Glu Val Val Lys Cys Leu Pro Val Thr Ala Pro Glu
                245                 250                 255

Asn Gly Lys Ile Val Ser Ser Ala Met Glu Pro Asp Arg Glu Tyr His
                260                 265                 270

Phe Gly Gln Ala Val Arg Phe Val Cys Asn Ser Gly Tyr Lys Ile Glu
                275                 280                 285

Gly Asp Glu Glu Met His Cys Ser Asp Asp Gly Phe Trp Ser Lys Glu
    290                 295                 300

Lys Pro Lys Cys Val Glu Ile Ser Cys Lys Ser Pro Asp Val Ile Asn
305                 310                 315                 320

Gly Ser Pro Ile Ser Gln Lys Ile Ile Tyr Lys Glu Asn Glu Arg Phe
                325                 330                 335

Gln Tyr Lys Cys Asn Met Gly Tyr Glu Tyr Ser Glu Arg Gly Asp Ala
                340                 345                 350

Val Cys Thr Glu Ser Gly Trp Arg Pro Leu Pro Ser Cys Glu Asp Ser
                355                 360                 365

Thr Gly Lys Cys Gly Pro Pro Pro Pro Ile Asp Asn Gly Asp Ile Thr
                370                 375                 380

Ser Phe Pro Leu Ser Val Tyr Ala Pro Ala Ser Ser Val Glu Tyr Gln
385                 390                 395                 400

Cys Gln Asn Leu Tyr Gln Leu Glu Gly Asn Lys Arg Ile Thr Cys Arg
                405                 410                 415

Asn Gly Gln Trp Ser Glu Pro Pro Lys Cys Leu His Pro Cys Val Ile
                420                 425                 430

Ser Arg Glu Ile Met Glu Asn Tyr Asn Ile Ala Leu Arg Trp Thr Ala
                435                 440                 445

Lys Gln Lys Leu Tyr Ser Arg Thr Gly Glu Ser Val Glu Phe Val Cys
    450                 455                 460

Lys Arg Gly Tyr Arg Leu Ser Ser Arg Ser His Thr Leu Arg Thr Thr
465                 470                 475                 480

Cys Trp Asp Gly Lys Leu Glu Tyr Pro Thr Cys Ala Lys Arg
                485                 490
```

POLYPEPTIDES FOR INHIBITING COMPLEMENT ACTIVATION

BACKGROUND OF THE INVENTION

The complement system is an integral part of the innate immunity and contributes to the recognition and elimination of pathogens, clearance of apoptotic cells or immune complexes and modulation of the adaptive immune response (Ricklin et al. 2010, Carroll et al. 2011). Complement is composed of a number of plasma proteins produced mainly by the liver, normally circulating as zymogens or as membrane proteins and operates in plasma, in tissues, or within cells. The activation of the three complement pathways the classical (CP), the lectin (LP) or the alternative pathway (AP) each results in the formation of C3 convertases (C4b2a in the CP, LP or C3bBb in the AP) which catalyzes the cleavage of the central component of the complement system, C3, into the activation product C3b and the anaphylactic peptide C3a. Subsequently and in a cascade-like triggered reaction, pathogens are marked for destruction and a series of inflammatory responses is induced recruiting immune cells to fight infection and maintain homeostasis (reviewed in (Merle et al. 2015)). Both, inefficient activation or inefficient regulation of complement may be causative for or contribute to a number of infections or non-infectious diseases, including immunodeficiency, autoimmunity, chronic inflammation, thrombotic microangiopathy, graft rejection as well as renal and retinal diseases such as atypical hemolytic uremic syndrome (aHUS), C3 Glomerulopathies (C3G) and age-related macular degeneration (AMD) (Holers 2008).

The Alternative Pathway (AP)

While the CP and LP are triggered by certain recognition molecules, the AP is permanently active at a low level. This occurs by a mechanism called "tick-over", that is initiated by hydrolysis of the internal C3 thioester of the C3b-like molecule C3(H2O) to form its bioactive form. Together with the soluble Factor B (FB) and Factor D (FD), that cleaves C3(H2O) bound FB, fluid phase C3 convertase complexes (C3b(H20)Bb) are generated and native C3 molecules are cleaved and activated. Activated C3b binds covalently, via a thioester-containing domain (TED or C3d domain), to hydroxyl groups of any adjacent surfaces. On pathogens, C3b in the immediate proximity to the site of its generation is accumulated and further C3 convertases (C3bBb) are formed, thereby amplifying complement activation. The binding of a second C3b to the C3 convertase leads to the generation of the C5 convertase (C3bBbC3b) that initiates the cleavage of C5 into the potent immune effector molecule C5a and C5b. C5b recruits complement components C6, C7, C8 and C9 forming the C5b-9 terminal membrane attack complex (MAC) which results in lysis of pathogens (Ricklin et al. 2010, Carroll et al. 2011).

Regulation of the AP

The AP has to be precisely regulated to allow rapid elimination of opsonized cells and pathogens and to minimize unrestricted AP activation that may cause host tissue damage. Healthy host cells are usually protected from complement mediated attack by a number of membrane-bound or soluble proteins of the regulator of complement activation (RCA) family that act on different activation levels of the cascade, some of them having overlapping functionality, while others have unique complement regulatory properties (Zipfel et al. 2009).

The generation of new C3b is strictly controlled by RCA proteins acting as cofactors for Factor I (FI) mediated irreversible degradation of C3b into iC3b or by destabilization of the C3bBb convertase complexes (Decay Acceleration Activity, DAA). In addition, RCAs can interfere with C5 convertase activity, thereby controlling the cleavage of C5 into its activation products C5a and C5b or by factors binding to terminal complement complex (TCC) compounds thereby preventing insertion of the MAC complex in the membrane. Together with membrane cofactor protein (MCP or CD46), complement receptor 1 (CR1 or CD35), decay accelerating factor (DAF or CD55) membrane inhibitor of reactive lysis (MIRL, CD59) and the soluble factors vitronectin and clusterin and others, members of the Factor H/FHR protein family, in particular FH, supports regulation of complement in circulation and on surfaces to which it specifically binds.

The Factor H/FHR Protein Family

The factor H/FHR protein family comprises a group of highly related plasma proteins that includes the five complement Factor H-related proteins (FHRs), FHR1, FHR2, FHR3, FHR4, FHR5, Factor H (FH) and the spliced variant Factor H-like protein 1 (FHL-1). Each single gene of the family members is located on a distinct segment on human chromosome 1q32 within the RCA gene cluster (Skerka et al. 2013). While FH is the main regulator of the alternative pathway, the functions of the FHRs are not completely understood. It has been suggested that the interaction of FHR proteins modulate the complement regulatory activity on cell surfaces (Jozsi et al. 2015). In addition, their ability for homo- and hetero-oligomerization can increase the avidity of FHR1, FHR2 and FHR5 for their ligands. This has been proposed as a fine tuning like mechanism in the recognition and modulation of complement activation (Jozsi et al. 2015). However, some FH independent and unique complement regulatory properties have also been described for FHR1 and FHR2. Since FH, FHR1 and FHR2 can downregulate complement activation, they have been proposed as promising candidates to modulate complement activation under pathological conditions (Licht et al. 2005, Licht et al. 2006, Skerka et al. 2013, Haffner et al. 2015).

Among the FH/FHR protein family, FH is the most abundant complement protein circulating in plasma at concentrations of ~350-600 µg/ml. With a molecular weight of 155 kDa, the monomeric glycoprotein FH regulates the AP and the amplification loop of the complement pathways. FH consists of 20 repetitive short consensus repeat (SCR) domains and regulates the activation of C3 convertases in fluid phase as well as on cell surfaces. The N-terminal domains SCR1-4 contain the complement regulatory region of the protein. FH SCR1-4 binds C3b and thereby prevents the formation of the C3 and C5 convertases and facilitates the disassembly of already formed convertases by competing with FB for C3b binding (Weiler et al. 1976). Additionally, these domains are relevant for FH to act as a cofactor for FI mediated C3b inactivation (Gordon et al. 1995, Rodriguez de Cordoba et al. 2004, Alexander et al. 2007, de Cordoba et al. 2008). The C-terminus of FH (SCR 19-20) primarily represents the binding recognition domain that interacts with C3b, C3d, pentraxins, extracellular matrix and cellular surfaces (Jarva et al. 1999, Oppermann et al. 2006, Hebecker et al. 2013). Binding of FH on cell surfaces or biological membranes is mediated by polyanionic structures like glycosaminoglycans (GAG) (e.g. heparin) or sialic acids, and regulates local complement activation on endogenous cells, such as glomerular endothelial cells or the glomerular basement membrane (GBM) (Jozsi et al. 2004, Ferreira et al. 2006, Jozsi et al. 2007, Blaum et al. 2015).

FHR1 is composed out of five SCRs (Skerka et al. 1991) and has two isoforms. Two glycosylated forms (FHR1α ~41 and FHR1β ~37 kDa) with either one or two carbohydrate side chains circulate in human plasma with a concentration of about 100 μg/ml. FHR1 has a high C-terminal sequence homology to FH and C-terminal SCR1 and SCR2 have high amino acid identity to SCR1 and SCR2 of FHR2 (97% and 100%, respectively) and to SCR1 and SCR2 of FHR5 (91% and 83%, respectively). FHR1 regulates C5-convertase activity and inhibits complement activation while C3-convertase activity is uninfluenced. N-terminal SCR1-2 binds to C5 and C5b6, whereas the C-terminal SCR3-5 binds to C3b, C3d and heparin. Supposedly, FHR inhibits C5 activation and cleavage into C5a and C5b by binding of SCR1-2 to C5. In addition FHR1 is a terminal pathway regulator and inhibits the assembly of the MAC, presumably by binding of SCR1-2 to C5b6 complex (Heinen et al. 2009).

FHR2 consists of four SCRs (Skerka et al. 1992) displaying amino acid identity to SCR 6-7 and 19-20 of FH. The N-terminal SCR1 of FHR2 is almost identical to FHR1 and FHR5 and allows the formation of homodimers and heterodimers with FHR1, but not with FHR5. FHR2 circulates in the human plasma at concentrations of about 50 μg/ml. FHR2 regulates complement activation, presumably via a mechanism in which FHR2 bound C3 convertases do not cleave the substrate C3. Interestingly, FHR2 hardly competes off factor H from C3b. FHR2 does not compete with FH for binding to C3b at physiological concentrations (Goicoechea de Jorge et al. 2013).

FHR1 like FHR2 and FHR5 each contain a conserved dimerization interface built up of residues Tyr34, Ser36 and Tyr39 located in SCR1 that play a key role in the assembling and facilitates homo- and heterodimer formation transmitted by a tight antiparallel binding of the N-terminus. In addition to its regulatory functions, FHRs prevent FH binding (or compete off FH) to C3b or host/pathogen cell surfaces under certain conditions causing a deregulation (activation) of complement (Jozsi et al. 2015). The formation of multimeric FHR complexes might increase local concentration thereby increasing avidity and/or affinity toward its substrate or toward surfaces that are to be regulated by FHRs. It has been suggested that deregulation may be intensified under pathophysiological conditions for example due to abnormal multimerisation of FHRs in C3 Glomerulopathies which enhances ligand binding and FH competition (Goicoechea de Jorge et al. 2013).

AP Associated Diseases

Dysregulation of the AP caused by mutations, dysfunctional polymorphisms in complement components and regulators such as FH or antibodies that promote activation of the AP are highly associated with diseases such as atypical hemolytic uremic syndrome (aHUS) (Noris et al. 2009) or C3 glomerulopathies (C3G) (Barbour et al. 2013) age-related macular degeneration (AMD) (Kawa et al. 2014) or paroxysomal nocturnal hemoglobinuria (PNH) (Holers 2008). Beside these a pathogenic role for the AP has been shown or postulated for IgA-nephropathy (Maillard et al. 2015), systemic lupus erythematosus—(SLE) (Wilson et al. 1976), ischemia-reperfusion (IR) damage or transplant rejection, rheumatoid arthritis (RA) and many others (Holers 2008) (Ricklin et al. 2013).

Atypical HUS and C3G are master models for AP related disease. In aHUS, mutations in either components of the AP or its regulators (C3, FB, FI, FH, FHR1 or MCP) or anti-FH antibodies lead to uncontrolled complement activation and ultimately formation of C5b-9 and endothelial cell damage. This is accompanied by glomerular thrombotic microangiopathy and acute renal failure, historically resulting in death or terminal renal failure in more than 60% of the patients. In C3G, which progresses to terminal renal failure in more than 50% of the patients within ten years, complement deposits are found in or on the glomerular basement membrane. AP activation in C3G is also caused by mutations in complement genes, especially FH, or by autoantibodies (C3 nephritic factor) affecting the C3 convertase (Loirat et al. 2011, Sethi et al. 2012).

Therapeutic Options in Complement Related Diseases

Established therapeutic options in the treatment of aHUS or C3G are limited and include plasmapheresis or substitution with fresh frozen plasma (FFP), immunosuppressive treatment and renal transplantation with a high risk of recurrence of the underlying disease (Braun et al. 2005, Lu et al. 2012, Cataland et al. 2014, Masani et al. 2014). Currently, a number of complement-targeting therapeutics are under investigation and might offer treatment options in the future (Wagner et al. 2010, Ricklin et al. 2013). Among them, eculizumab, a humanized monoclonal anti-05 antibody, blocks TCC formation and has recently been approved for the treatment of aHUS (Zimmerhackl et al. 2010). For C3G, no therapeutic regime has been established yet (Masani et al. 2014). The application of eculizumab in C3G patients led to a partial response in only some patients (Bomback et al. 2012).

Blockade of the late effector functions of complement can be obtained if the cleavage of C5 by the C5 convertase is prevented. The therapeutic monoclonal antibody eculizumab binds human C5 and inhibits its activation into the potent anaphylatoxin C5a and the initiator of the terminal complement pathway C5b by C5 convertase (Parker et al. 2007). Thereby, eculizumab blocks inflammatory signaling and cell lysis by MAC formation, but leaves the C3 convertases and uncontrolled production of C3a unaffected. Eculizumab showed significant improvement in clinical outcome and has been accepted for treatment of complement-mediated diseases including paroxysmal nocturnal hemoglobinuria (PNH) (Hillmen et al. 2006) and aHUS (Zuber et al. 2012).

The central position of C3 in the complement cascade makes it an attractive target for therapeutic interventions, consequently inhibitors acting at the level of C3 have also been designed. Compstatin is a small peptide of 13 amino acids that is being tested pre-clinically (Mastellos et al. 2015). Structural studies have revealed that compstatin binds to the ß-chain of C3 and C3b and blocks the interaction with C3 convertases. Thereby, compstatin inhibits the activation of C3 and also further amplification of the cascade and prevents downstream formation of complement effectors. Compstatin does not prevent cleavage of C3 by proteases such as thrombin nor the "activation" of C3 into C3(H2O) via "Tick-Over" (Ricklin et al. 2015) and has shown efficacy in complement blocking in vitro and in animal models including extracorporeal circulation, sepsis, and PNH. Another approach is the exploitation of our natural panel of RCAs like FH or soluble CR1 or to improve their efficiency by combination of selected domain modules (Ricklin et al. 2013). TT30, containing FH SCR1-5 and CR2 SCR1-4 is designed to accumulate preferentially at sites already under complement-mediated attack. TT30 interacts simultaneously with C3b and C3d merging the functionality of fluid phase FH binding to C3b with CR2 interaction to C3d on the surface of host cells. TT30 showed significant improvement in models of AMD, ischemia/reperfusion injury, and PNH (Merle et al. 2015,). Mini-FH molecules, containing SCR1-4 or SCR 1-5 and SCR19-20 bind C3b and C3d with high affinity and show better efficacy compared to native FH in in vitro models of aHUS and PNH (Hebecker et al. 2013, Schmidt et al. 2013). However, in FH deficient mice, showing a C3G-like phenotype, the therapeutic effects of mini-FH and a murine analog of TT30 on plasma alternative pathway control were comparatively modest, in association with a short half-life (Nichols et al. 2015, Ruseva et al. 2015).

Eculizumab is approved for the application in aHUS and PNH. It blocks the cleavage of C5 by C5 convertase nonspecifically. Patients under eculizumab therapy are at risk for developing severe infectious diseases, especially meningococcal infections like meningitis. On the other hand blockade of TCC formation does not influence C3 convertase activation. This might lead to a sustained production of the anaphylatoxin C3a in treated patients and to continuous deposition of C3 cleavage products in kidneys, as seen in C3G patients under eculizumab therapy. Additionally deposits of the eculizumab antibodies were found in kidney biopsies in eculizumab treated patients (Herlitz et al. 2012). Until now long term effects of theses deposits are not investigated.

Blockade of only C5 convertase might also not be sufficient in all AP related diseases. Single case reports on the effectiveness of eculizumab in C3G patients show only benefits in some patients mostly as a partial remission (Bomback et al. 2012, Legendre et al. 2013).

New complement regulators like compstatin, mini-FH or TT30 try to influence the complement activation on the level of C3 convertase. These developments are under investigation in a preclinical stadium. Eculizumab and other regulators that are currently under development are targeting either C5 convertase or C3 convertase.

SUMMARY OF THE INVENTION

The inventors of this application found that complement activation can be effectively blocked by acting on multiple effector sites in the complement cascade (inhibition of C3/C5-convertases, inhibition of C5 cleavage and TCC formation) simultaneously. This leads to a more effective regulation of AP (and CP) activity, allowing a fine tuning between AP (CP) down regulation and prevention of anaphylatoxin release, thereby presumably reducing unwanted side effects.

Furthermore, the inventors found that a dimerization motif within a regulator, built up of selected domain modules 1) increases regulatory activity by the formation of multimeric complexes and 2) is resistant to FHR mediated deregulation.

The present invention therefore relates to the following embodiments (1) to (24)
(1) A polypeptide comprising an inhibitory C3 convertase effector domain and an inhibitory C5 convertase (C5 binding) effector domain.
(2) The polypeptide of item 1, wherein said inhibitory C3 convertase effector domain confers C3 convertase inhibition by decay-accelerating and cofactor activity.
(3) The polypeptide of item 1 or 2, wherein said polypeptide has decay-accelerating and cofactor activity.
(4) The polypeptide of any one of items 1 to 3, wherein said inhibitory C3 convertase effector domain is a fragment of Factor H (FH).
(5) The polypeptide of any one of the preceding items, wherein said inhibitory C3 convertase effector domain comprises or consists of Short Consensus Repeats (SCRs) 1 to 4 of FH.
(6) The polypeptide of any one of items 1 to 3, wherein said inhibitory C3 convertase effector domain comprises or consists of SCRs 1-4 of FHR2.
(7) The polypeptide of any one of the preceding items, wherein said inhibitory C5 convertase effector domain is a fragment of Factor H-related protein 1 (FHR1).
(8) The polypeptide of any one of the preceding items, wherein said inhibitory C5 convertase effector domain comprises or consists of SCR1 and SCR2 of FHR1.
(9) The polypeptide of any one of the preceding items, wherein C5 activation and cleavage into C5a and C5b is inhibited by binding of the polypeptide to C5.
(10) The polypeptide of any one of the preceding items, further comprising a domain that is capable of binding to cellular surfaces.
(11) The polypeptide of any one of the preceding items, wherein said domain that is capable of binding to cellular surfaces comprises SCR19 and SCR20 of FH.
(12) The polypeptide of any one of the preceding items, wherein said polypeptide is a multimer.
(13) The polypeptide of item 12, comprising at least one dimerization motif from SCR1 of FHR1.
(14) The polypeptide of any one of the preceding items, wherein said polypeptide is capable of inhibiting TCC (C5b-9) formation.
(15) The polypeptide of item 14, wherein said TCC formation is inhibited by binding of the polypeptide to C5b-6.
(16) A polypeptide having the structure A-B-C, wherein A is an inhibitory C5 convertase effector domain as defined in any one of the preceding items, B is an inhibitory C3 convertase effector domain as defined in any one of the preceding items, and C is absent or a domain that is capable of binding to cellular surfaces as defined in any one of the preceding items.
(17) The polypeptide of item 16, wherein A and B are fused directly or via a linker.
(18) The polypeptide of item 16 or 17, wherein B and C are fused directly or via a linker.
(19) The polypeptide as defined in any one of the preceding items for use in the treatment or prevention of a disorder related to or associated with the complement system.
(20) The polypeptide for use according to item 19, wherein said disorder related to or associated with the complement system is selected from the group consisting of atypical hemolytic uremic syndrome (aHUS), thrombotic microangiopathy (TMA), C3 glomerulopathy (C3G), IgA nephropathy, systemic lupus erythematosus nephritis, transplant rejection, paroxysmal nocturnal hemoglobinuria (PNH), age-related macular degeneration (AMD), infectious diseases, sepsis, SIRS, trauma injury, ischemia/reperfusion damage and myocardial infarction.
(21) A nucleic acid encoding the polypeptide of any one of items 1 to 18.
(22) A plasmid or vector comprising the nucleic acid of item 21.
(23) A cell comprising the nucleic acid of item 21 or the plasmid or vector of item 22.
(24) A method of producing the polypeptide of any one of items 1 to 18, comprising culturing the cells of item 23 in a culture medium under conditions that allow expression of the polypeptide, and recovering the polypeptide from the cells or the culture medium.

DETAILED DESCRIPTION

The invention pertains to a polypeptide comprising an inhibitory C3 convertase effector domain, an inhibitory C5 convertase effector domain (C5 binding domain), and optionally an inhibitory TCC formation domain and/or a dimerization motif.

Figure 4:
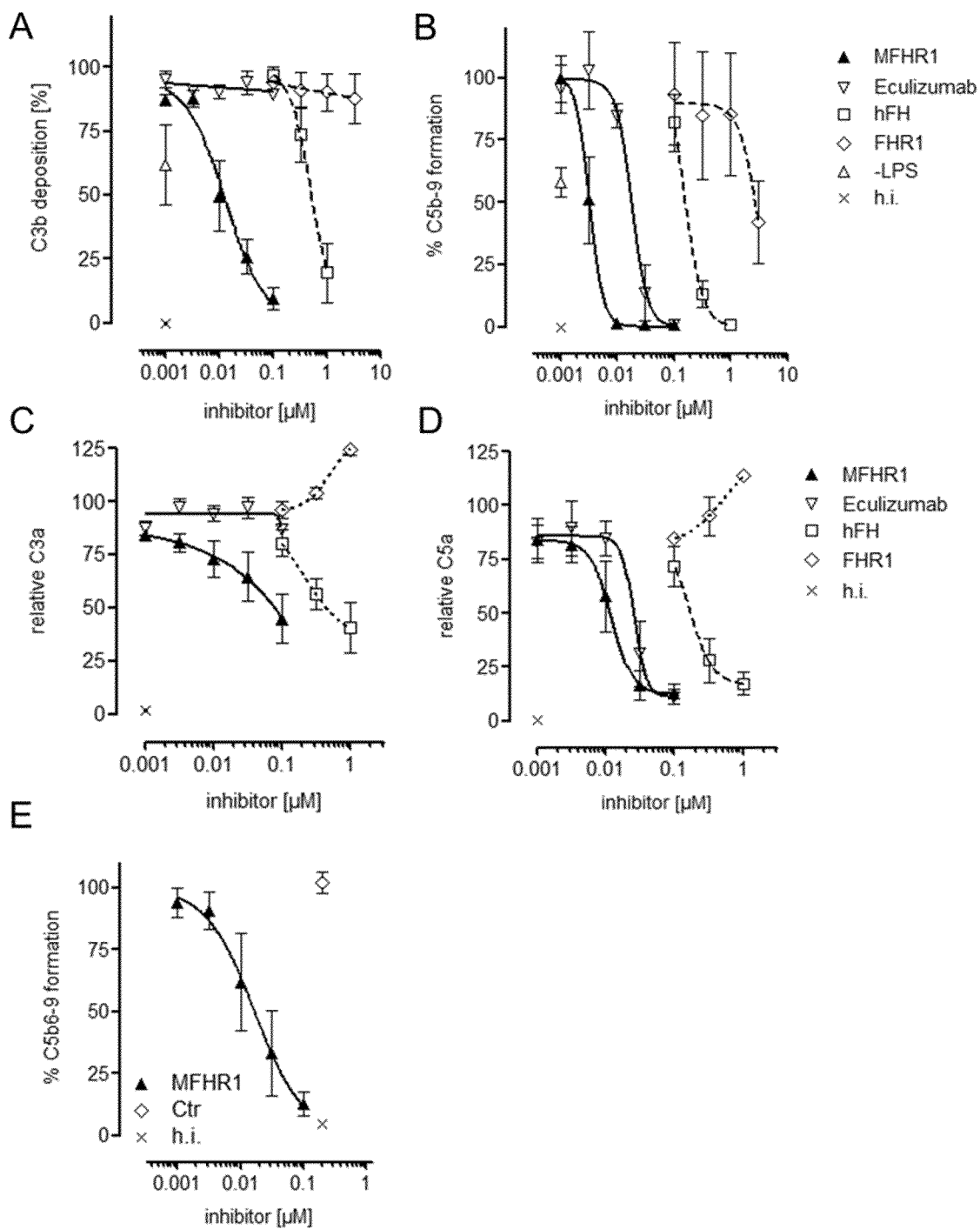
FIG. 4. MFHR1 inhibits complement alternative pathway (AP) and classical pathway (CP) activation and reduces anaphylatoxin release in human serum at clinically relevant levels. MFHR1, hFH, FHR1 or Eculizumab were added into human serum and A) C3b depositions or B) C5b-9 complex formation was measured following alternative pathway (AP) activation was proceeded by LPS using specific buffer conditions. A) MFHR1 reduces surface C3b depositions with higher efficiency than hFH as measured by ELISA using anti-human C3 and HRP-labelled secondary antibodies. As expected, eculizumab did not inhibit C3b depositions. B) MFHR1 inhibits C5b-9 with higher efficiency than hFH or eculizumab as determined using the complement AP-ELISA (WIESLAB®). Untreated control serum was set to 100% for each individual experiment. Data represent single values from n=4 assays±SEM using sera of 4 individual healthy donors. In addition, MFHR1 efficiently blocks generation of C) C3a and D) C5a as assayed in the supernatant of AP activated sera using specific C3a, C5a ELISA (Quidel) (n=3 assays±SEM). E) Inhibition of classical pathway (CP) by MFHR1 was assessed using the complement CP-ELISA (WIESLAB®). AP activity of untreated control serum was set to 100% for each individual experiment. Data represent single values from n=3 assays±SEM using sera of 3 individual healthy 3 donors. See Table 1 for calculated IC50 values.

An "inhibitory C3 convertase effector domain" in connection with the present invention refers to an amino acid sequence capable of inhibiting C3 convertase, i.e. of inhibiting C3 convertase formation. Inhibition of C3 convertase is typically present if deposition of C3b is inhibited or if there is a reduced formation of C3a after complement alternative pathway activation relative to a control. Formation of C3b and C3a can be determined in assays as depicted in FIG. 4A or FIG. 4C, respectively. In another embodiment, the inhibitory C3 convertase effector domain has C3 convertase decay-accelerating activity and cofactor activity. C3 convertase decay-accelerating activity can be determined in an assay as depicted in FIG. 2B. Cofactor activity can be determined in an assay as depicted in FIG. 2C-2D.

In certain embodiments the inhibitory C3 convertase effector domain is fragment of FH. In accordance with the present invention, FH denotes a protein having at least 70% sequence identity with the amino acid sequence as shown in SEQ ID NO:1. Preferably, the FH has an amino acid sequence identity with the amino acid sequence as shown in SEQ ID NO:1 of at least 80%, more preferably of at least 90%, more preferably of at least 95%. Most preferably, FH comprises or consists of an amino acid sequence as shown in SEQ ID NO:1.

The comparison of sequences and determination of percent identity (and percent similarity) between two amino acid sequences can be accomplished using any suitable program, e.g. the program "BLAST 2 SEQUENCES (blastp)" (Tatusova et al. (1999) FEMS Microbiol. Lett. 174, 247-250) with the following parameters: Matrix BLOSUM62; Open gap 11 and extension gap 1 penalties; gap x_dropoff50; expect 10.0 word size 3; Filter: none.

The C3 convertase effector domain preferably comprises or consists of SCR1-4 of FH. In one embodiment, the C3 convertase effector domain comprises or consists of amino acids 19-264 of SEQ ID NO:1.

In another embodiment, the inhibitory C3 convertase effector domain is fragment of FHR2. In accordance with the present invention, FHR2 denotes a protein having at least 70% sequence identity with the amino acid sequence as shown in SEQ ID NO:3. Preferably, the amino acid sequence of the FHR2 has a sequence identity with the amino acid sequence as shown in SEQ ID NO:3 of at least 80%, more preferably of at least 90%, more preferably of at least 95%. Most preferably, FHR2 comprises or consists of an amino acid sequence as shown in SEQ ID NO:3.

The C3 convertase effector domain may comprise or consist of SCR1-4 of FHR2. In one embodiment, the C3 convertase effector domain comprises or consists of amino acids 22-268 of SEQ ID NO:3.

Figure 3:
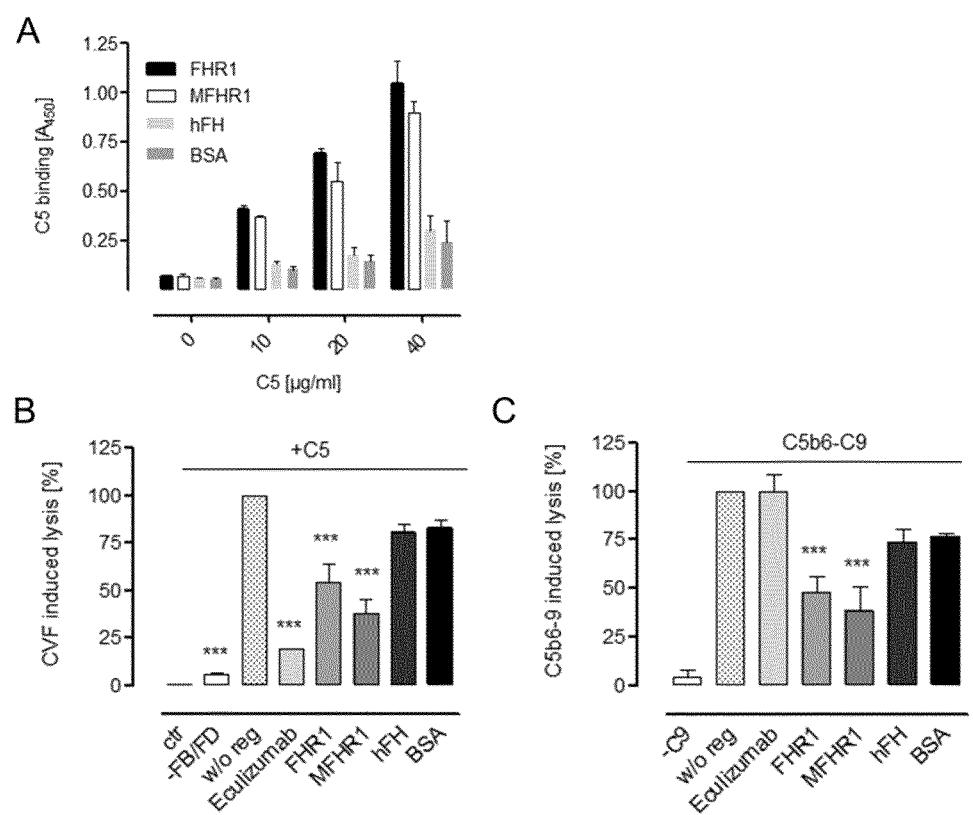
FIG. 3. MFHR1 binds C5 and regulates terminal pathway activation by inhibition of the C5 convertase/C5 cleavage and MAC formation. A) MFHR1 binds to C5 as determined by ELISA. Equimolar amounts of MFHR1, full length FHR1, hFH or BSA (133 nM) were immobilized to Nunc plates and incubated with increasing concentrations (10, 20, 40 µg/ml) of C5. Binding was detected using monoclonal C5 antibodies and HRP-labelled secondary antibodies. Data are mean±SD from n=3 experiments B) MFHR1 inhibits AP activation by blockade of C5 cleavage. Cobra venom factor (CVF) C5 convertase was generated on sheep erythrocytes (sE) after adding Factor B (FB) and Factor D (FD). Hemolysis was induced after adding C5, C6, C7, C8 and C9 components and detected at 414 nm. Preincubation of C5 with FHR1, MFHR1 or Eculizumab significantly inhibited hemolysis while hFH or BSA showed now inhibition. Controls without CVF convertase (−FB/FD) or C5 did not induce hemolysis. C) MFHR1 inhibits formation of the membrane attack complex (MAC) on sE. MAC formation on sE was induced by incubation with C5b6, C7, C8 and C9 components and detected by hemolysis of cells. Preincubation of C5b6 with MFHR1, FHR1 or Eculizumab inhibited hemolysis at significant levels compared to hFH or BSA. Samples without C9 did not induce hemolysis. In B and C control without regulator (w/o) was set as 100%. All data represent mean values ±SD of 3 separate experiments. ***P<0.001 vs. w/o control, one-way ANOVA with Bonferroni multiple comparison test.

An "inhibitory C5 convertase effector domain" in connection with the present invention refers to an amino acid sequence capable of inhibiting C5 convertase. Inhibition of C5 convertase (prevention of C5 cleavage) is typically present if there is a reduced formation of C5a. Formation of C5a can be determined in an assay as depicted in FIG. 4D. In an alternative experimental approach binding of an inhibitory effector domain to C5 is shown (FIG. 3 A). This prevents C5 cleavage to C5a and C5b by experimental C5 convertases and inhibits MAC formation and lysis of cells as depicted in (FIG. 3 B).

Figure 5:
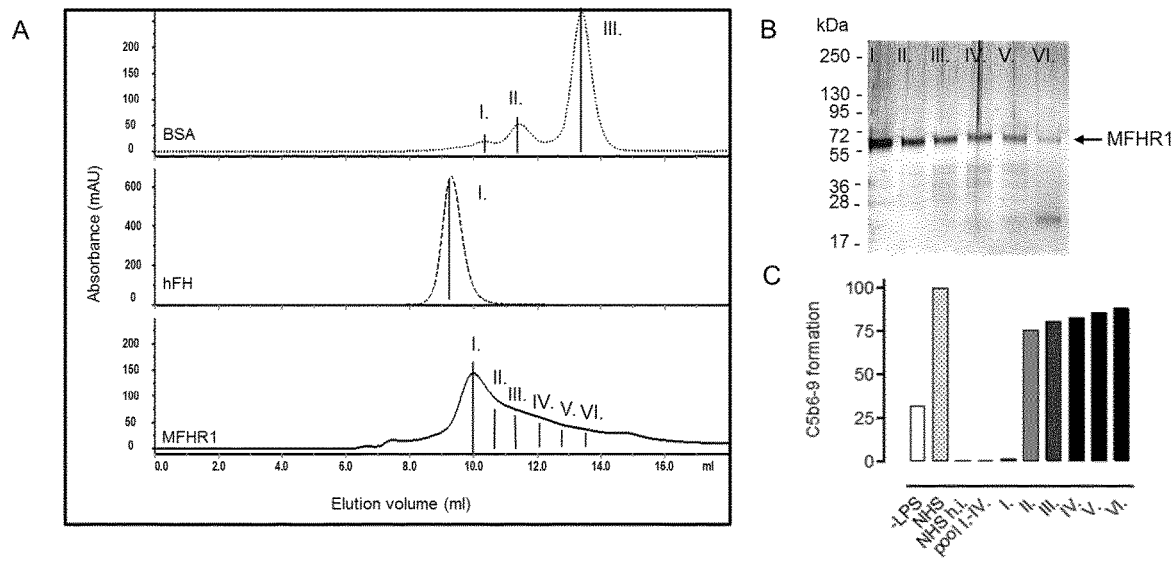
FIG. 5. Multimeric complexes increase AP regulatory activity of MFHR1 in human serum. A) Size exclusion chromatography (Superdex 200 10/300 GL) of bovine serum albumin (BSA), serum plasma derived FH (hFH) and MFHR1. The three compositions of BSA mixture presented different retention volumes based on molecular mass, which was I. BSA trimer (198 kDa, 10.35 ml), II. BSA dimer (132 kDa, 11.45 ml) and III. BSA monomer (66 kDa, 13.4 ml). Under the same condition, hFH (9.3 ml) showed that the peak of protein species migrates as dimeric proteins at approximately 300 kDa. MFHR1 showed a peak (I.) at retention volume of 10 ml indicating that MFHR1 migrates predominantly in a multimeric state in the fluid phase. Theoretical trimer (II. 10.7), dimer (III. 11.4) intermediates (IV.-V.) or monomeric (IV. 13.5) MFHR1 are indicated in the elution profile. B) Analysis of MFHR1 after elution from SEC column as performed in A. 20 µl protein from fractions was loaded on a 10% SDS-PAGE and silver stained C) Afterwards, single or pooled MFHR1 SEC fractions were added into human serum at 10 nM and AP activation was proceeded by incubation in LPS coated wells using AP specific buffer conditions. Regulatory efficiency of MFHR1 fractions was analyzed by measuring C5b-9 complex formation. AP activity of untreated control serum was set to 100%.

In certain embodiments the inhibitory C5 convertase effector domain is fragment of FHR1. In accordance with the present invention, FHR1 denotes a protein having at least 70% sequence identity with the amino acid sequence as shown in SEQ ID NO:2. Preferably, the amino acid sequence of the FHR1 has a sequence identity with the amino acid sequence as shown in SEQ ID NO:2 of at least 80%, more preferably of at least 90%, more preferably of at least 95%. Most preferably, FHR1 comprises or consists of an amino acid sequence as shown in SEQ ID NO:2. Besides binding to C5 and preventing C5 cleavage by C5 convertases, SCR 1-2 from FHR1 comprise a dimerization motif, which leads to multimerisation of MFHR1 amplifying function of the polypeptide as shown in FIG. 5. Besides C5 convertase inhibition, SCR 1-2 from FHR1 inhibit MAC formation by binding C5b-6 (FIG. 3C).

The inhibitory C5 convertase effector domain preferably comprises or consists of SCR1 and SCR2 of FHR1. In one embodiment, the inhibitory C5 convertase effector domain comprises or consists of amino acids 22-142 of SEQ ID NO:2.

The inhibitory C3 convertase effector domain, the inhibitory C5 convertase and the inhibitory MAC formation effector domain may be fused directly or via a linker. The linker may be a peptidic linker or a non-peptidic linker. Preferably, the linker consists of 1 to 100 amino acids, more preferably of 1 to 50 amino acids, more preferably of 1 to 20 amino acids, more preferably of 1 to 10 amino acids, most preferably of 1 to 5 amino acids. The linker sequence is typically heterologous to amino acid sequence of the C3 convertase effector domain and to the amino acid sequence of the inhibitory C5 convertase effector domain.

The polypeptide of the invention may have the structure A-B, wherein A is the C3 convertase effector domain as defined herein, and B is a C5 convertase effector domain as defined herein. In another embodiment, the polypeptide of the invention may have the structure B-A, wherein A is the C3 convertase effector domain as defined herein, and B is a C5 convertase effector domain as defined herein.

In a particular embodiment, the polypeptide of the invention comprises or consists of an amino acid sequence selected from the group consisting of SEQ ID NO:4, SEQ ID NO:5, SEQ ID NO:6 and SEQ ID NO:7.

In certain embodiments the polypeptide of the invention comprises a third domain, said third domain having cell surface binding properties. Preferably, said third domain comprises or consists of a fragment of FH. More preferably, the third domain comprises or consists of SCR19 and SCR20 of FH. In one embodiment, the third domain comprises or consists of amino acids 1107-1230 of SEQ ID NO:1.

The polypeptide of the invention may have the structure A-B-C, wherein A is the C5 convertase effector domain as defined herein, B is a C3 convertase effector domain as defined herein, and C is the third domain as defined herein. In another embodiment, the polypeptide of the invention may have the structure A-C-B, B-A-C, B-C-A, C-A-B, or C-B-A, wherein the meanings of A, B and C are as defined herein. The order of the letters A, B and C indicates the sequence from N-terminus to C-terminus of the polypeptide, e.g. in A-B-C, domain A is at the N-terminus, and domain C is at the C-terminus.

The third domain can be fused directly to the C3 convertase effector domain and/or to the C5 effector domain and MAC effector domain, or via a linker as defined hereinabove.

In a particular embodiment, the polypeptide of the invention comprises or consists of the amino acid sequence as shown in SEQ ID NO:8. In another embodiment, the polypeptide of the invention comprises or consists of the amino acid sequence as shown in SEQ ID NO:9.

The polypeptide of the invention can be used to treat or prevent disorders related to and/or associated with the complement system. These disorders include, but are not limited to, atypical hemolytic uremic syndrome (aHUS), thrombotic microangiopathy (TMA), C3 glomerulopathy (C3G), IgA nephropathy, systemic lupus erythematosus nephritis, humoral rejections in kidney transplanted patients, tissue damage after ischemia-reperfusion events, e.g. after renal transplantation, excessive complement activation, tissue damage, e.g. under hemodialysis, Paroxysmal nocturnal hemoglobinuria (PNH), age-related macular degeneration (AMD), infectious diseases, sepsis, SIRS, trauma injury, myocardial infarction are diseases and conditions where complement activation is made responsible for additional local or systemic damage.

Preferably, the disorder to be treated or prevented is selected from the group consisting of aHUS, TMA, C3G, IgA nephropathy, systemic lupus erythematosus nephritis, PNH and AMD.

The invention further provides nucleic acids encoding the polypeptide of the invention, which can be inserted into suitable plasmids and vectors for expression in host cells.

The nucleic acid encoding the polypeptide to be expressed can be prepared according to methods known in the art. Based on the cDNA sequences of FH (NCBI Reference Sequence: NM_000186.3) FHR1 (NCBI Reference Sequence: NM_002113.2) and FHR2 (NCBI Reference Sequence: NP_005657.1) recombinant DNA encoding the above-mentioned polypeptides can be designed and generated.

Constructs in which the cDNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis. Typically, the cells to be provided are obtained by introducing the nucleic acid encoding the polypeptide into suitable host cells.

Any host cell susceptible to cell culture and to expression of polypeptides may be utilized in accordance with the present invention. In certain embodiments, the host cell is mammalian. In other embodiments, the host cell is an insect cell, e.g. an Sf9 cell), or a physcomitrella cell (e.g. *Physcomitrella patens*). Alternatively, the host cell may be a bacterial cell.

In general, it will typically be desirable to isolate and/or purify glycoproteins expressed according to the present invention. In certain embodiments, the expressed glycoprotein is secreted into the medium and thus cells and other solids may be removed, as by centrifugation or filtering for example, as a first step in the purification process.

The expressed polypeptide may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference).

One of ordinary skill in the art will appreciate that the exact purification technique will vary depending on the character of the polypeptide to be purified, the character of the cells from which the polypeptide is expressed, and/or the composition of the medium in which the cells were grown.

Another aspect of the invention is a pharmaceutical composition comprising the polypeptide of the invention, and a pharmaceutically acceptable excipient or carrier. The pharmaceutical composition may comprise the polypeptide in an effective amount for treating or preventing a complement-related disorder in a subject.

Therapeutic formulations of the polypeptide of the invention suitable in the methods described herein can be prepared for storage as lyophilized formulations or aqueous solutions by mixing the glycoprotein having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

The pharmaceutical compositions of the present invention may be formulated for oral, sublingual, intranasal, intraocular, rectal, transdermal, mucosal, topical or parenteral administration. Parenteral administration may include intradermal, subcutaneous, intramuscular (i.m.), intravenous (i.v.), intraperitoneal (i.p.), intra-arterial, intramedullary, intracardiac, intraarticular (joint), intrasynovial, intracranial, intraspinal, and intrathecal (spinal fluids) injection or infusion, preferably intraperitoneal (i.p.) injection in mouse and intravenous (i.v.) in human. Any device suitable for parenteral injection or infusion of drug formulations may be used for such administration. For example, the pharmaceutical composition may be contained in a sterile pre-filled syringe.

Determination of the effective dosage, total number of doses, and length of treatment with a soluble polypeptide of the invention is well within the capabilities of those skilled in the art, and can be determined using a standard dose escalation study. The dosage of a soluble polypeptide of the invention to be administered will vary according to the particular soluble polypeptide, the subject, and the nature and severity of the disease, the physical condition of the subject, the therapeutic regimen (e.g., whether a second therapeutic agent is used), and the selected route of administration; the appropriate dosage can be readily determined by a person skilled in the art.

Summary of the Amino Acid Sequences:

| SEQ ID NO: | Description |
|---|---|
| 1 | Amino acid sequence of FH |
| 2 | Amino acid sequence of FHR1 |
| 3 | Amino acid sequence of FHR2 |
| 4 | Amino acid sequence of construct MMFHR1 with His tag His-tag - FHR1(SCR1-2)-FH(SCR1-4) |
| 5 | Amino acid sequence of construct MMFHR1 without His tag FHR1(SCR1-2)-FH(SCR1-4) |
| 6 | Amino acid sequence of construct FHR1-FHR2 with His tag His-tag - FHR1(SCR1-2)-FHR2(SCR1-4) |
| 7 | Amino acid sequence of construct FHR1-FHR2 without His tag FHR1(SCR1-2)-FHR2(SCR1-4) |
| 8 | Amino acid sequence of construct MFHR1 with His tag His-tag - FHR1(SCR1-2)-FH(SCR1-4)-FH(SCR19-20) |

-continued

| SEQ ID NO: | Description |
|---|---|
| 9 | Amino acid sequence of construct MFHR1 without His tag FHR1(SCR1-2)-FH(SCR1-4)-FH(SCR19-20) |

EXAMPLES

Figure 1:
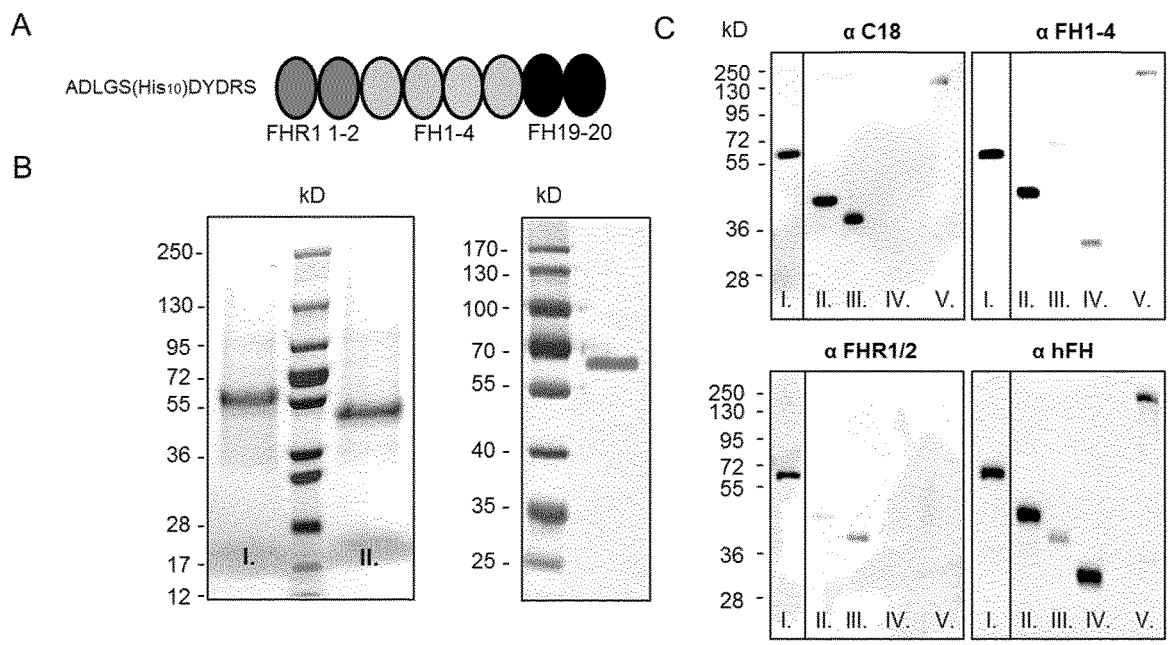
FIG. 1: Structure and characterization of MFHR1. A) Structural assembly of MFHR1. MFHR1 is a fusion protein composed of SCR1-2 of FHR1 (FHR1 1-2)N-terminally linked to SCR1-4 and SCR19-20 of hFH termed as FH1-4 and FH19-20, respectively. A penta-histidine tag (N-terminal) was used as means for purification. FHR1-2 contains a dimerization motif, inhibits C5 convertase activity and MAC assembly. FH has decay acceleration and cofactor activity (FH1-4) and binding sites for C3b and cell surfaces (FH19-20). B) SDS-PAGE and Coomassie (left) or silver (right) staining of MFHR1 purified from supernatants of baculovirus infected SF9 cells via Ni-affinity and size exclusion chromatography. MFHR1 appears with the calculated molecular weight of 58.65 kDa under reducing conditions. Faster mobility of MFHR1 under non-reducing conditions (Coomassie stain, right lane) indicates the presence of disulfide bounds. C) Immunodetection using polyclonal anti-human FH, anti-FH1-4 or monoclonal anti-C18 and anti-FHR1-2 antibodies indicates the correct integrity of FHR1-2, FH1-4 and FH20 in recombinant MFHR1 (I.). Recombinant FH1-4; 19-20 (II.), full-length FHR1 (III.), FH1-4 (IV.) or human plasma derived hFH (V.) served as controls.

MFHR1 consists of the N-terminal FH regulatory active domains SCR1-4 (C3/C5 convertase decay accelerating- and cofactor activity) with C-terminal surface recognition domains (SCR19-20) of FH in combination with the N-terminal domains of FHR1 (SCR1-2) [FIG. 1]. FHR1 is the only known endogenous complement regulator of the C5 convertase. FHR1 SCR1-2 binds to C5 and thereby inhibits C5 cleavage into C5a and C5b. Additionally, FHR1 SCR1-2 inhibits the terminal complement pathway by binding to C5b6. Through the combination of these domains the complement activation is inhibited at multiple effector sites of the cascade (C3b degradation, inhibition of C3/C5-convertases, inhibition of C5 cleavage and C5b-9 formation). This also leads to the suppression and formation of the anaphylatoxins C3a and C5a, which are thought to contribute in disease progression in AP related diseases.

To produce MFHR1, cDNA fragments containing the requested sequence of the FH and FHR1 domains mentioned above were amplified by PCR and subsequently assembled by self-priming overlap PCR. The DNA was cloned into the pFastbac gp67-10×His baculo expression vector and MFHR1 was expressed in SF9 insect cells. The amino acid sequence of MFHR1 is shown in SEQ ID NO:8. The purification of the protein was performed by affinity chromatography and size exclusion chromatographie. SDS-PAGE and Commassie or silver stained gel showed a single 58.65 kDa band corresponding to the calculated molecular weight of MFHR1 [FIG. 1B]. The successful fusion of FHR1 SCR1-2 and FH SCR 1-4 and SCR 19-20 was confirmed by immunodetection using specific antibodies for the detection of FHR1 derived domains SCR1-2, anti-FH1-4 for detection of FH derived domains 1-4, monoclonal anti-C18 for detection of FH derived domain 20 and polyclonal FH antibodies [FIG. 1C].

Figure 2:
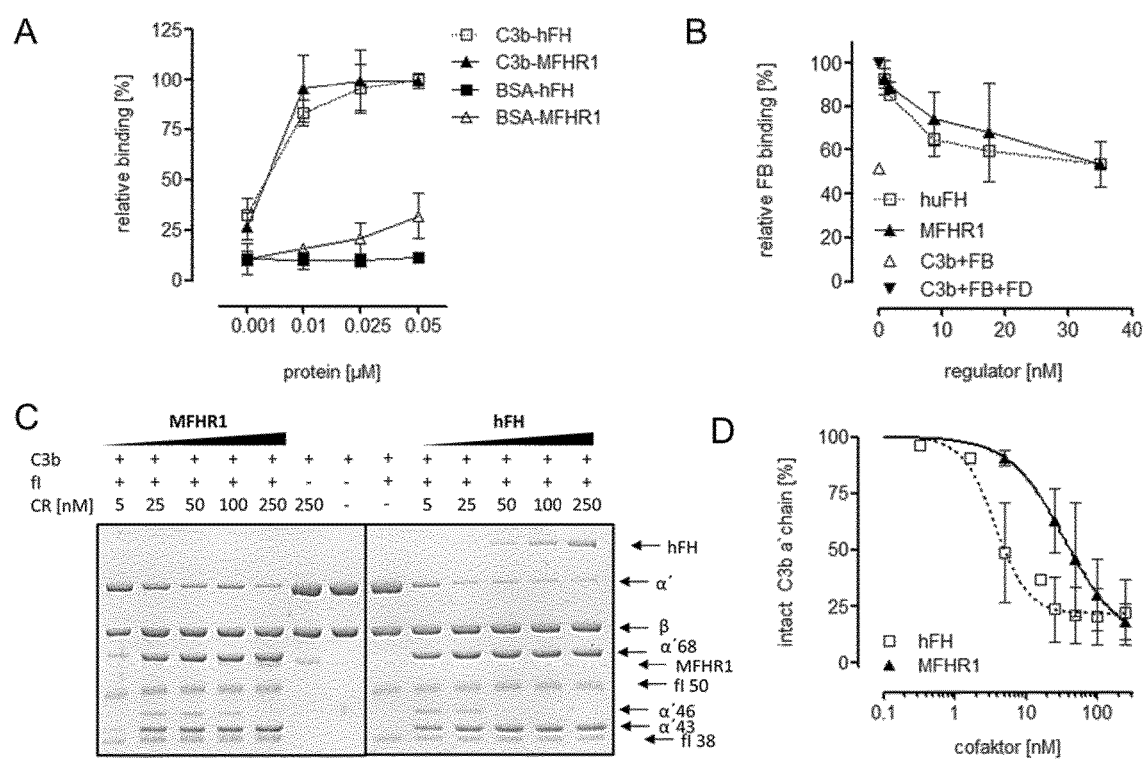
FIG. 2. MFHR1 binds to C3b, displays cofactor activity and dissociates C3 convertases. A) Interaction of MFHR1 to C3b was analyzed by ELISA. C3b was immobilized on microtiter plates and serial dilutions of MFHR1 or hFH were added and binding was detected using anti-FH primary and HRP-labelled anti-goat secondary antibodies. BSA coated wells were used as controls. Data are mean±SD from n=3 experiments. Maximum binding of hFH to C3b was set to 100% relative binding. B) MFHR1 efficiently dissociates C3bBb (C3 convertase) complexes. Convertases were assembled on microtiter plates in presence of C3b, Factor B (FB) and Factor D (FD) and hFH or MFHR1 were added and incubated at 37° C. Intact C3bBb and dissociation of these complexes was measured by the relative amount of FB. OD450 values of control wells (C3b+FB+FD without regulators) were set to 100%. Negative control was performed without adding FD. Data are mean±SD from n=3 experiments. C) MFHR1 displays cofactor activity. Cofactor testing was performed by incubation of C3b and Factor I (FI) with increasing concentrations of MFHR1 or hFH (5-250 nM) for 30 min at 37° C. SDS-PAGE and Coomassie blue staining was used to visualise α-chain cleavage and α'68, α'43 and α'46 fragments. D) For quantification of cofactor activity, C3b α-chain band intensity was determined by densitometry and intact C3b α-chain was normalized to ß-chain and set to 100%. Data represent mean values ±SD from n=5 experiments.
Figure 7:
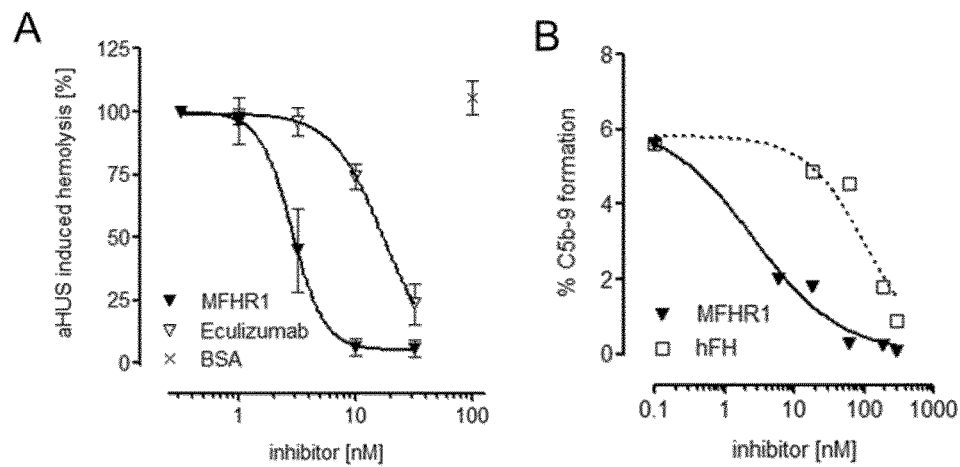
FIG. 7. MFHR1 reduces uncontrolled complement activation in modeling treatment of atypical haemolytic uremic syndrome (aHUS) and C3 Glomerulopathy (C3G) A) Mutations in FH may be causative for familial aHUS and loss of complement regulation in sera of these patients mediate hemolysis if added to sheep erythrocytes (sE). MFHR1 added to serum of an aHUS patient (pat. #1 FH R1215Q (Gerber et al. 2003)) protects sE from complement mediated MAC formation and lysis with higher efficiency than eculizumab. Data represent mean values ±SD from n=3 experiments. B) Serum C3 is ubiquitously increased in C3G duo to an excessive complement activation and inhibition uncontrolled complement activity may offer an alternative treatment option in C3G. MFHR1 added to serum of a C3Neph positive patient efficiently inhibits AP activation and C5b-9 formation after LPS stimulation.

MFHR1 binds to C3b [FIG. 2A], dissociates C3 convertases [FIG. 2B] and displays cofactor activity [FIG. 2C-2D]. In contrast to plasma purified FH (FHplasma), FHR1 and MFHR1 show the ability to bind C5, mediated by SCR1-2 from FHR1 [FIG. 3A]. FHR1 and MFHR1 regulate terminal pathway activation by inhibition of the C5 convertase/C5 cleavage [FIG. 3B] and MAC formation [FIG. 3C]. This demonstrates that our novel fusion protein MFHR1 not only retains the complement regulatory activity of FH [FIG. 2] and FHR1 [FIG. 3], but moreover, combines the properties of both. MFHR1 inhibits aHUS serum induced hemolysis of sheep erythrocytes more efficient than eculizumab, demonstrating that, in addition to its regulatory activity, surface recognition derived from FH domains 19-20 is retained in MFHR1 [FIG. 7A]. The high potency of MFHR1 was further emphasized in ELISA based complement activity assays. Following activation of the complement cascade in human serum spiked with MFHR1, its AP regulatory activity was determined by measuring C3b depositions [FIG. 4A] or C5b6-9 [FIG. 4B] and its CP regulatory efficiency was determined by measuring C5b6-9 using the WIESLAB® CP-ELISA [FIG. 4E]. The addition of MFHR1 to normal human serum (NHS) or serum from a C3G patient (patient under relapse, C3Nef autoantibody positive) efficiently inhibits complement activation in a dose dependent manner [FIG. 4A-B, 4E, 7B]. As in the hemolytic assay, MFHR1 showed higher inhibitory efficiency on a molar basis than hFH (Table 1), eculizumab and other relevant inhibitors that are under investigation in a preclinical stadium (IC50 values summarized in Table 1). Furthermore, we demonstrate that MFHR1 inhibits the generation of C3a [FIG. 4C] and C5a [FIG. 4D] in human serum more efficiently than eculizumab.

Figure 6:
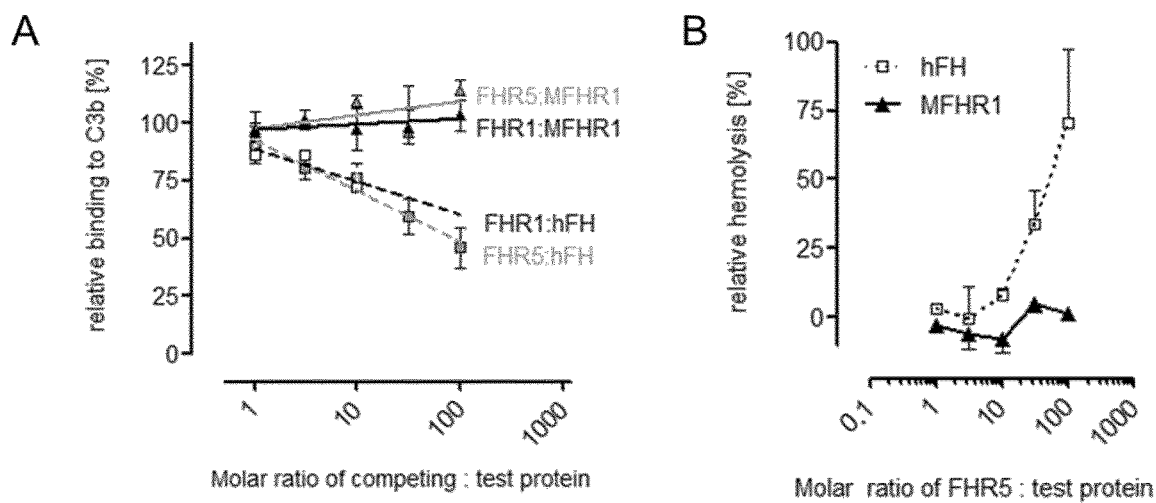
FIG. 6. MFHR1 is resistant to deregulation by FHR1 and FHR5. A) MFHR1 binding to C3b is not competitively inhibited by FHR1 or FHR5. MFHR1 (triangles) or hFH (square) (termed as test protein) was added to C3b coated microtiter plates alone or with increasing concentrations of FHR1 (black line) or FHR5 (grey line) ranging from equimolar amounts to 100-fold excess. MFHR1 or hFH bound to C3b was detected using specific antibodies. Average of 3 independent assays with SD is shown. B) MFHR1 mediated protection of sheep erythrocytes (sE) from serum induced AP-activation is not attenuated by FHR5, while AP regulatory function of hFH was dose dependent deregulated by FHR5. MFHR1 or hFH was used at concentrations that reduce FH-depleted serum induced lysis of sE to 50% and increasing concentrations FHR5 ranging from equimolar amounts to 100-fold excess were added. Hemolysis was determined at 414 nm and data are expressed as relative increase over samples where no FHR5 has been added. Data represent single values from n=3 assays±SEM.

The use of a dimerization motif (mediated by SCR1 of FHR1) facilitates the generation of multimeric complexes of MFHR1. We showed that multimeric complexes have higher regulatory activity, presumably by increasing local concentration of the regulators [FIG. 5]. Furthermore, MFHR1 is resistant to FHR mediated deregulation [FIG. 6A-B].

Figure 8:
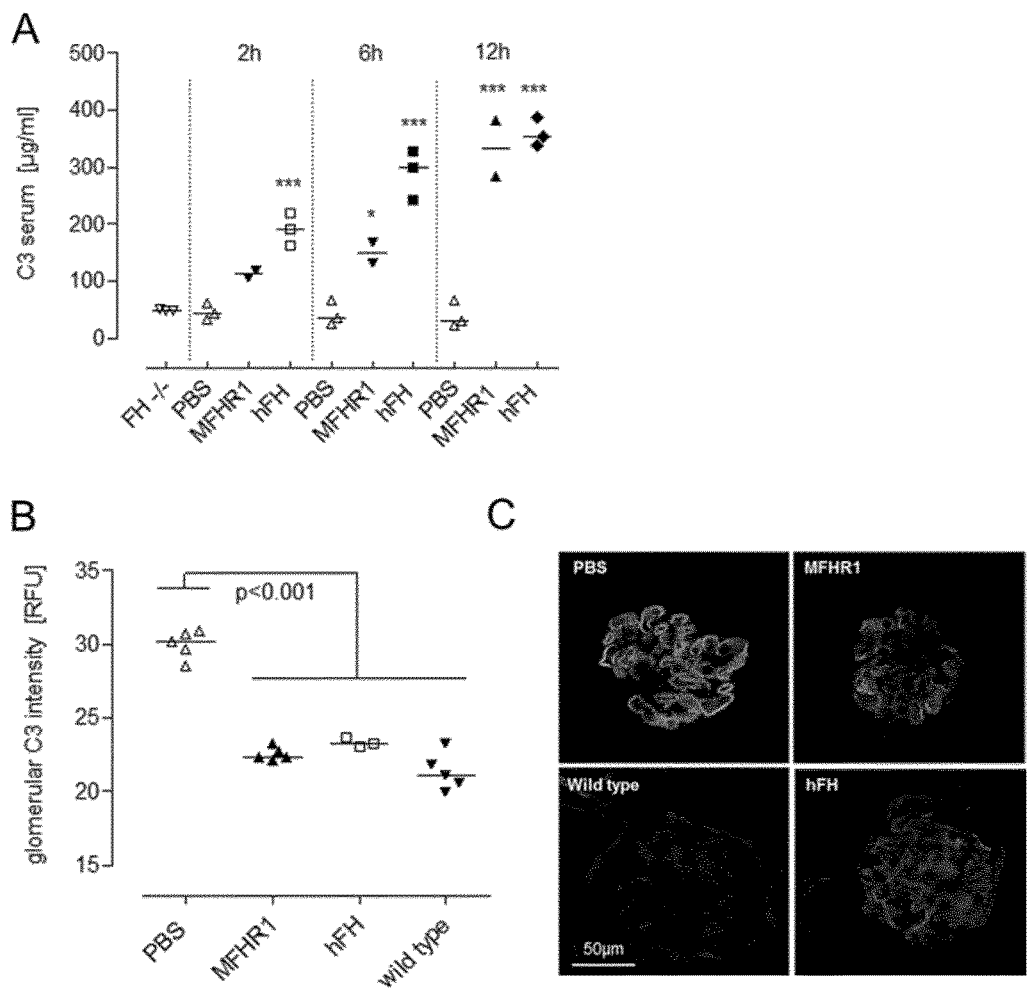
FIG. 8. MFHR1 shows significant therapeutic benefit against uncontrolled complement activation in C3 Glomerulopathy (C3G) in vivo. A-C) FH-deficient mice (FH-/-) develop abnormal glomerular C3 accumulation and low serum C3 levels due AP overactivation thus providing a useful C3G model for testing therapeutic efficiency of complement targeted drugs. A) MFHR1 significantly increases C3 serum levels at indicated time points after intraperitoneal injection of 0.5 mg MFHR1 at comparable levels to hFH. Mean values are shown as bars with plotted individual data points. B) MFHR1 significantly reduces abnormal glomerular C3 accumulation. Glomerular C3 fluorescence intensity was determined 24 hours after administration of MFHR1, hFH or PBS treated FH-/- mice. Sections of untreated wild-type mice were used as negative control. Means are shown as bars±SD with plotted individual data points expressed as arbitrary fluorescence units (AFU). C) Representative images of glomerular C3 depositions. Scale bars; 50 μm. ***P<0.001 vs. PBS group, one-way ANOVA with Bonferroni test.

Therapeutic value of MFHR1 was proven in two modeling treatment approaches in vitro and a murine model of C3G in vivo. The addition of MFHR1 efficiently reduces uncontrolled complement activation in sera of aHUS [FIG. 7A] and C3G [FIG. 7B] patients. In FH−/− deficient mice, showing a C3G-like phenotype, the administration of MFHR1 resulted in the rapid normalization of plasma C3 levels [FIG. 8 A] and resolution of the glomerular C3 deposition [FIG. 8 B-C].

TABLE 1

Summary of estimated IC50 values for inhibitory activity in human serum

| Regulator | AP ELISA (IC50) | | CP ELISA (IC50) |
|---|---|---|---|
| | C3b depositions | C5b-9 | C5b-9 |
| MFHR1 | 0.015 ± 0.009 | 0.0033 ± 0.001 | 0.021 ± 0.01 |
| hFH | 0.537 ± 0.238 (0.53*) | 0.177 ± 0.08 (3.0 ± 1.6**) | n.t. |
| Eculizumab | n.e. | 0.015 ± 0.0025 | n.t. |
| mini-FH | 0.05 ± 0.027 (0.04*) | 0.016 ± 0.013 | n.t. |
| TT30 | 0.014*** | 0.04 ± 0.005** | 2.1 ± 0.7** |
| Compstatin | 1.42# | 1.07# | n.t. |

Values are in μM.
IC50 values were calculated using log(inhibitor) vs. response --variable slope equation after transformation of the X data to Log X using GraphPad Prism software,
n.t. = not tested, n.e. = no effect.
Bold letters, A G Häffner, *Schmidt et al. 2013, Hareli et al. 2011, *Schmidt et al. 2015, #Gorham et al. 2013.

Taken together, our results demonstrate that combinatorial approaches to intercept complement activation on multiple effector sites in the complement cascade (C3b degradation, inhibition of C3/C5-convertases, inhibition of C5 cleavage and TCC formation) simultaneously and by its ability to multimerize (or respectively both) has several beneficial advantages compared to "conventional" approaches in order to improve regulators of complement activation. MFHR1, comprising different functional properties from FH and FHR1 regulates complement activity on the level of C3 and C5 convertases and by blocking the terminal complement pathway and is likely more active compared to FH or eculizumab or other published clinical relevant complement inhibitors. Notably, MFHR1 is particularly resistant to deregulation by FHR1 and FHR5 and multimeric complexes may increase its regulatory efficiency.

REFERENCES

Alexander, J. J. and R. J. Quigg (2007). "The simple design of complement factor H: Looks can be deceiving." Mol Immunol 44(1-3): 123-132.

Barbour, T. D., M. C. Pickering and H. T. Cook (2013). "Recent insights into C3 glomerulopathy." Nephrol Dial Transplant 28(7): 1685-1693.

Blaum, B. S., J. P. Hannan, A. P. Herbert, D. Kavanagh, D. Uhrin and T. Stehle (2015). "Structural basis for sialic acid-mediated self-recognition by complement factor H." Nature chemical biology 11(1): 77-82.

Bomback, A. S., R. J. Smith, G. R. Barile, Y. Zhang, E. C. Heher, L. Herlitz, M. B. Stokes, G. S. Markowitz, V. D. D'Agati, P. A. Canetta, J. Radhakrishnan and G. B. Appel (2012). "Eculizumab for dense deposit disease and C3 glomerulonephritis." Clinical journal of the American Society of Nephrology: CJASN 7(5): 748-756.

Braun, M. C., D. M. Stablein, L. A. Hamiwka, L. Bell, S. M. Bartosh and C. F. Strife (2005). "Recurrence of membranoproliferative glomerulonephritis type II in renal allografts: The North American Pediatric Renal Transplant Cooperative Study experience." J Am Soc Nephrol 16(7): 2225-2233.

Carroll, M. V. and R. B. Sim (2011). "Complement in health and disease." Adv Drug Deliv Rev 63(12): 965-975.

Cataland, S. R. and H. M. Wu (2014). "Diagnosis and management of complement mediated thrombotic microangiopathies." Blood reviews 28(2): 67-74.

de Cordoba, S. R. and E. G. de Jorge (2008). "Translational mini-review series on complement factor H: genetics and disease associations of human complement factor H." Clin Exp Immunol 151(1): 1-13.

Ferreira, V. P., A. P. Herbert, H. G. Hocking, P. N. Barlow and M. K. Pangburn (2006). "Critical role of the C-terminal domains of factor H in regulating complement activation at cell surfaces." J Immunol 177(9): 6308-6316.

Goicoechea de Jorge, E., J. J. Caesar, T. H. Malik, M. Patel, M. Colledge, S. Johnson, S. Hakobyan, B. P. Morgan, C. L. Harris, M. C. Pickering and S. M. Lea (2013). "Dimerization of complement factor H-related proteins modulates complement activation in vivo." Proc Natl Acad Sci USA 110(12): 4685-4690.

Gordon, D. L., R. M. Kaufman, T. K. Blackmore, J. Kwong and D. M. Lublin (1995). "Identification of complement regulatory domains in human factor H." J Immunol 155(1): 348-356.

Haffner, K., S. Michelfelder and M. Pohl (2015). "Successful therapy of C3Nef-positive C3 glomerulopathy with plasma therapy and immunosuppression." Pediatric nephrology.

Hebecker, M., M. Alba-Dominguez, L. T. Roumenina, S. Reuter, S. Hyvarinen, M. A. Dragon-Durey, T. S. Jokiranta, P. Sanchez-Corral and M. Jozsi (2013). "An engineered construct combining complement regulatory and surface-recognition domains represents a minimal-size functional factor H." J Immunol 191(2): 912-921.

Herlitz, L. C., A. S. Bomback, G. S. Markowitz, M. B. Stokes, R. N. Smith, R. B. Colvin, G. B. Appel and V. D. D'Agati (2012). "Pathology after eculizumab in dense deposit disease and C3 GN." J Am Soc Nephrol 23(7): 1229-1237.

Hillmen, P., N. S. Young, J. Schubert, R. A. Brodsky, G. Socie, P. Muus, A. Roth, J. Szer, M. O. Elebute, R. Nakamura, P. Browne, A. M. Risitano, A. Hill, H. Schrezenmeier, C. L. Fu, J. Maciejewski, S. A. Rollins, C. F. Mojcik, R. P. Rother and L. Luzzatto (2006). "The complement inhibitor eculizumab in paroxysmal nocturnal hemoglobinuria." The New England journal of medicine 355(12): 1233-1243.

Holers, V. M. (2008). "The spectrum of complement alternative pathway-mediated diseases." Immunological reviews 223: 300-316.

Jarva, H., T. S. Jokiranta, J. Hellwage, P. F. Zipfel and S. Meri (1999). "Regulation of complement activation by C-reactive protein: targeting the complement inhibitory activity of factor H by an interaction with short consensus repeat domains 7 and 8-11." J Immunol 163(7): 3957-3962.

Jozsi, M., T. Manuelian, S. Heinen, M. Oppermann and P. F. Zipfel (2004). "Attachment of the soluble complement regulator factor H to cell and tissue surfaces: relevance for pathology." Histol Histopathol 19(1): 251-258.

Jozsi, M., M. Oppermann, J. D. Lambris and P. F. Zipfel (2007). "The C-terminus of complement factor H is essential for host cell protection." Mol Immunol 44(10): 2697-2706.

Jozsi, M., A. Tortajada, B. Uzonyi, E. Goicoechea de Jorge and S. Rodriguez de Cordoba (2015). "Factor H-related proteins determine complement-activating surfaces." Trends in immunology 36(6): 374-384.

Kawa, M. P., A. Machalinska, D. Roginska and B. Machalinski (2014). "Complement system in pathogenesis of AMD: dual player in degeneration and protection of retinal tissue." Journal of immunology research 2014: 483960.

Legendre, C. M., C. Licht, P. Muus, L. A. Greenbaum, S. Babu, C. Bedrosian, C. Bingham, D. J. Cohen, Y. Delmas, K. Douglas, F. Eitner, T. Feldkamp, D. Fouque, R. R. Furman, O. Gaber, M. Herthelius, M. Hourmant, D. Karpman, Y. Lebranchu, C. Mariat, J. Menne, B. Moulin, J. Nurnberger, M. Ogawa, G. Remuzzi, T. Richard, R. Sberro-Soussan, B. Severino, N. S. Sheerin, A. Trivelli, L. B. Zimmerhackl, T. Goodship and C. Loirat (2013). "Terminal complement inhibitor eculizumab in atypical hemolytic-uremic syndrome." The New England journal of medicine 368(23): 2169-2181.

Licht, C., S. Heinen, M. Jozsi, I. Loschmann, R. E. Saunders, S. J. Perkins, R. Waldherr, C. Skerka, M. Kirschfink, B. Hoppe and P. F. Zipfel (2006). "Deletion of Lys224 in regulatory domain 4 of Factor H reveals a novel pathomechanism for dense deposit disease (MPGN II)." Kidney Int 70(1): 42-50.

Licht, C., A. Weyersberg, S. Heinen, L. Stapenhorst, J. Devenge, B. Beck, R. Waldherr, M. Kirschfink, P. F. Zipfel and B. Hoppe (2005). "Successful plasma therapy for atypical hemolytic uremic syndrome caused by factor H deficiency owing to a novel mutation in the complement cofactor protein domain 15." American journal of kidney diseases: the official journal of the National Kidney Foundation 45(2): 415-421.

Loirat, C. and V. Fremeaux-Bacchi (2011). "Atypical hemolytic uremic syndrome." Orphanet J Rare Dis 6: 60.

Lu, D. F., M. Moon, L. D. Lanning, A. M. McCarthy and R. J. Smith (2012). "Clinical features and outcomes of 98 children and adults with dense deposit disease." Pediatric nephrology 27(5): 773-781.

Maillard, N., R. J. Wyatt, B. A. Julian, K. Kiryluk, A. Gharavi, V. Fremeaux-Bacchi and J. Novak (2015). "Current Understanding of the Role of Complement in IgA Nephropathy." J Am Soc Nephrol 26(7): 1503-1512.

Manuelian, T., J. Hellwage, S. Meri, J. Caprioli, M. Noris, S. Heinen, M. Jozsi, H. P. Neumann, G. Remuzzi and P. F. Zipfel (2003). "Mutations in factor H reduce binding affinity to C3b and heparin and surface attachment to endothelial cells in hemolytic uremic syndrome." J Clin Invest 111(8): 1181-1190.

Masani, N., K. D. Jhaveri and S. Fishbane (2014). "Update on membranoproliferative GN." Clinical journal of the American Society of Nephrology: CJASN 9(3): 600-608.

Mastellos, D. C., D. Yancopoulou, P. Kokkinos, M. Huber-Lang, G. Hajishengallis, A. R. Biglarnia, F. Lupu, B. Nilsson, A. M. Risitano, D. Ricklin and J. D. Lambris (2015). "Compstatin: a C3-targeted complement inhibitor reaching its prime for bedside intervention." European journal of clinical investigation 45(4): 423-440.

Merle, N. S., S. E. Church, V. Fremeaux-Bacchi and L. T. Roumenina (2015). "Complement System Part I—Molecular Mechanisms of Activation and Regulation." Frontiers in immunology 6: 262.

Nichols, E. M., T. D. Barbour, I. Y. Pappworth, E. K. Wong, J. M. Palmer, N. S. Sheerin, M. C. Pickering and K. J. Marchbank (2015). "An extended mini-complement factor H molecule ameliorates experimental C3 glomerulopathy." Kidney Int.

Noris, M. and G. Remuzzi (2009). "Atypical hemolytic-uremic syndrome." The New England journal of medicine 361(17): 1676-1687.

Oppermann, M., T. Manuelian, M. Jozsi, E. Brandt, T. S. Jokiranta, S. Heinen, S. Meri, C. Skerka, O. Gotze and P. F. Zipfel (2006). "The C-terminus of complement regulator Factor H mediates target recognition: evidence for a compact conformation of the native protein." Clin Exp Immunol 144(2): 342-352.

Parker, C. J., S. Kar and P. Kirkpatrick (2007). "Eculizumab." Nature reviews. Drug discovery 6(7):515-516.

Ricklin, D., G. Hajishengallis, K. Yang and J. D. Lambris (2010). "Complement: a key system for immune surveillance and homeostasis." Nature immunology 11(9): 785-797.

Ricklin, D. and J. D. Lambris (2013). "Progress and Trends in Complement Therapeutics." Advances in experimental medicine and biology 735: 1-22.

Ricklin, D. and J. D. Lambris (2015). "Therapeutic control of complement activation at the level of the central component C3." Immunobiology.

Rodriguez de Cordoba, S., J. Esparza-Gordillo, E. Goicoechea de Jorge, M. Lopez-Trascasa and P. Sanchez-Corral (2004). "The human complement factor H: functional roles, genetic variations and disease associations." Mol Immunol 41(4): 355-367.

Ruseva, M. M., T. Peng, M. A. Lasaro, K. Bouchard, S. Liu-Chen, F. Sun, Z. X. Yu, A. Marozsan, Y. Wang and M. C. Pickering (2015). "Efficacy of Targeted Complement Inhibition in Experimental C3 Glomerulopathy." J Am Soc Nephrol.

Schmidt, C. Q., H. Bai, Z. Lin, A. M. Risitano, P. N. Barlow, D. Ricklin and J. D. Lambris (2013). "Rational engineering of a minimized immune inhibitor with unique triple-targeting properties." J Immunol 190(11): 5712-5721.

Sethi, S. and F. C. Fervenza (2012). "Membranoproliferative glomerulonephritis—a new look at an old entity." The New England journal of medicine 366(12): 1119-1131.

Skerka, C., Q. Chen, V. Fremeaux-Bacchi and L. T. Roumenina (2013). "Complement factor H related proteins (CFHRs)." Mol Immunol 56(3): 170-180.

Skerka, C., R. D. Horstmann and P. F. Zipfel (1991). "Molecular cloning of a human serum protein structurally related to complement factor H." J Biol Chem 266(18): 12015-12020.

Skerka, C., C. Timmann, R. D. Horstmann and P. F. Zipfel (1992). "Two additional human serum proteins structurally related to complement factor H. Evidence for a family of factor H-related genes." J Immunol 148(10): 3313-3318.

Wagner, E. and M. M. Frank (2010). "Therapeutic potential of complement modulation." Nature reviews. Drug discovery 9(1): 43-56.

Weiler, J. M., M. R. Daha, K. F. Austen and D. T. Fearon (1976). "Control of the amplification convertase of complement by the plasma protein beta1H." Proc Natl Acad Sci USA 73(9): 3268-3272.

Wilson, M. R., C. M. Arroyave, R. M. Nakamura, J. H. Vaughan and E. M. Tan (1976). "Activation of the alternative complement pathway in systemic lupus erythematosus." Clin Exp Immunol 26(1): 11-20.

Zimmerhackl, L. B., J. Hofer, G. Cortina, W. Mark, R. Wurzner, T. C. Jungraithmayr, G. Khursigara, K. O. Kliche and W. Radauer (2010). "Prophylactic eculizumab after renal transplantation in atypical hemolytic-uremic syndrome." The New England journal of medicine 362 (18): 1746-1748.

Zipfel, P. F. and C. Skerka (2009). "Complement regulators and inhibitory proteins." Nat Rev Immunol 9(10): 729-740.

Zuber, J., F. Fakhouri, L. T. Roumenina, C. Loirat, V. Fremeaux-Bacchi and H. C. G. French Study Group for a (2012). "Use of eculizumab for atypical haemolytic uraemic syndrome and C3 glomerulopathies." Nature reviews. Nephrology 8(11): 643-657.

The invention claimed is:

1. A polypeptide having the structure A-B-C, wherein A comprises SCR1 and SCR2 of FHR1, B comprises SCRs 1 to 4 of FH, and C is absent or a domain that is capable of binding to cellular surfaces.

2. The polypeptide of claim 1, wherein A and B are fused directly or via a linker.

3. The polypeptide of claim 1, wherein B and C are fused directly or via a linker.

4. A method of treating atypical hemolytic uremic syndrome (aHUS) or C3 glomerulopathy (C3G) which comprises administering to a patient in need thereof, a polypeptide comprising Short Consensus Repeats (SCRs) 1 to 4 of Factor H FH) and SCR1 and SCR2 of Factor H-related protein 1 (FHR1).

5. A nucleic acid encoding the polypeptide of claim 1.

6. A plasmid or vector comprising the nucleic acid of claim 5.

7. A cell comprising the nucleic acid of claim 5.

8. A method of producing a polypeptide of comprising an inhibitory C3 convertase effector domain and an inhibitory C5 convertase effector domain, which comprises culturing the cells of claim 7 in a culture medium under conditions that allow expression of the polypeptide, and recovering the polypeptide from the cells or the culture medium.

9. The polypeptide of claim 1, wherein the SCRs 1 to 4 of FH comprises amino acids 19-264 of SEQ ID NO: 1.

10. The polypeptide of claim 1, wherein the SCR1 and SCR2 of FHR1 comprises amino acids 22-142 of SEQ ID NO: 2.

* * * * *